US008450247B2

(12) United States Patent
Peelle et al.

(10) Patent No.: US 8,450,247 B2
(45) Date of Patent: May 28, 2013

(54) CELL DISPLAY LIBRARIES

(75) Inventors: Beau R. Peelle, Manhattan Beach, CA (US); Angela M. Belcher, Cambridge, MA (US); Karl Dane Wittrup, Cambridge, MA (US); Eric Krauland, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1064 days.

(21) Appl. No.: 11/051,481

(22) Filed: Feb. 7, 2005

(65) Prior Publication Data

US 2006/0003387 A1        Jan. 5, 2006

Related U.S. Application Data

(60) Provisional application No. 60/541,757, filed on Feb. 5, 2004.

(51) Int. Cl.
*C40B 20/00* (2006.01)
*C40B 30/00* (2006.01)
*C40B 40/02* (2006.01)
*C07K 14/00* (2006.01)
*C07K 7/00* (2006.01)

(52) U.S. Cl.
USPC .................. 506/14; 506/2; 506/7; 530/300

(58) Field of Classification Search
USPC .................................. 506/2, 7, 14; 530/300
See application file for complete search history.

(56) References Cited

U.S. PATENT DOCUMENTS

| | | | |
|---|---|---|---|
| 5,316,922 A | 5/1994 | Brown et al. | |
| 5,866,344 A | 2/1999 | Beorgiou | |
| 5,935,823 A | 8/1999 | Fowlkes et al. | |
| 6,136,566 A | 10/2000 | Sands et al. | |
| 6,207,371 B1 | 3/2001 | Zambrowicz et al. | |
| 6,214,613 B1 | 4/2001 | Higuchi et al. | |
| 6,255,071 B1 | 7/2001 | Beach et al. | |
| 6,300,065 B1 | 10/2001 | Kieke et al. | |
| 6,406,840 B1 | 6/2002 | Li et al. | |
| 6,423,538 B1 | 7/2002 | Wittrup et al. | |
| 2003/0068900 A1 | 4/2003 | Belcher et al. | |
| 2003/0073104 A1 | 4/2003 | Belcher et al. | |
| 2003/0113714 A1 | 6/2003 | Belcher et al. | |
| 2003/0148380 A1 | 8/2003 | Belcher et al. | |
| 2003/0166010 A1 | 9/2003 | Affholter | |
| 2004/0127640 A1 | 7/2004 | Belcher et al. | |
| 2004/0171139 A1 | 9/2004 | Belcher et al. | |

FOREIGN PATENT DOCUMENTS

WO    WO 99/36569    *    7/1999
WO    WO 01/43869    *    6/2001

OTHER PUBLICATIONS

Furukawa et al., 2003, Affinity selection fo target cells form cell surface displayed libraries: a novel procedure using thermo-responsive magnetic nanoparticles, Appl. Microbiol. Biotechnol., 62: 478-483, 2003.*
Brown et al., 1997, Nature Biotechnology 15: 269-272.*
Kanno et al., 2000, Assembling of engineered IgG-binding protein on gold surface for highly oriented antibody immobilization, Journal of Biotechnology, 76: 207-214.*
Woodbury et al., 1998, Construction of biosensors using a gold-binding polypeptide and a miniature integrated surface Plasmon resonance sensor, Biosensors & Bioelectronics, 13: 1117-1126.*
Sanz et al., 1989, The smaller human VH gene families display remarkably little polymorphism, The EMBO Journal, 8(12): 3741-3748.*
U.S. Appl. No. 60/510,862, filed Oct. 15, 2003, Belcher et al.
U.S. Appl. No. 60/511,102, filed Oct. 15, 2003, Belcher et al.
U.S. Appl. No. 60/534,102, filed Jan. 5, 2004, Belcher et al.
U.S. Appl. No. 60/541,757, filed Feb. 5, 2004, Belcher et al.
U.S. Appl. No. 10/665,721, filed Sep. 22, 2003, Belcher et al.
U.S. Appl. No. 10/965,227, filed Oct. 15, 2004, Belcher et al.
U.S. Appl. No. 10/965,665, filed Oct. 15, 2004, Belcher et al.
Bannister, S. J., et al., "Glutathione excretion in response to heterologous protein secretion in *Saccharomyces cerevisiae*", *Biotechnol Bioeng.*, vol. 68, No. 4, pp. 389-395 (May 20, 2000).
Barbas, J., et al., "Conversion in the peptides coating cadmium:sulfide crystallites in *Candida glabrata*", *J Inorg Biochem.*, vol. 48, No. 2, pp. 95-105 (1992).
Bhatia, S. K., et al., "Rolling Adhesion Kinematics of Yeast Engineered To Express Selectins", *Biotechnol Prog.* vol. 19, No. 3, pp. 1033-1037 (Jun. 6, 2003).
Boder, E. T., et al., "Directed evolution of antibody fragments with monovalent femtomolar antigen-binding affinity", *Proc. Natl. Acad. Sci.* USA, vol. 97, No. 20, pp. 10701-10705 (Sep. 26, 2000).
Boder, E. T., et al., "Optimal screening of surface-displayed polypeptide libraries", *Biotechnol Prog.* vol. 14, No. 1, pp. 55-62 (Jan.-Feb. 1998).
Boder, E. T., et al., "Yeast Surface Display for Directed Evolution of Protein Expression, Affinity, and Stability", *Methods in Enzymol.*, vol. 328, pp. 430-444 (2000).
Boder, E.T., et al., "Yeast surface display for screening combinatorial polypeptide libraries", *Nat. Biotechnol.* vol. 15, No. 6, pp. 553-557 (Jun. 1997).
Braden, B. C., et al., "X-ray crystal structure of an anti-Buckminsterfullerent antibody Fab fragment: Biomolecular recognition of $C_{60}$", *Proc. Natl. Acad. Sci.* USA, vol. 97, No. 22, pp. 12193-12197 (2000).
Brown, S., Engineered iron oxide-adhesion mutants of the *Escherichia coli* phage λ receptor *Proc. Natl. Acad. Sci.* USA, vol. 89, pp. 8651-8655 (1992).
Brown, S., "A Genetic Analysis of Crystal Growth", *J. Mol Biol.*, vol. 299, pp. 725-735 (2000).
Brown, S., "Metal-recognition by repeating polypeptides", *Nature Biotechnol.*, vol. 15, pp. 269-272. (1997).

(Continued)

*Primary Examiner* — Amber D Steele
(74) *Attorney, Agent, or Firm* — Foley & Lardner LLP

(57) ABSTRACT

Eukaryotic cell display libraries for use in panning processes comprising expressed biomolecules for specific and selective binding and enrichment to solid material surfaces including, for example, metal, magnetic, and semiconducting surfaces. Display can be regulated. Peptide and protein display on yeast cells are preferred. Solid materials can be fabricated in the presence of cell display libraries which have been subjected to panning against the solid materials. Nanoparticles can be grown in the presence of the biomolecules from reactive precursors. The nanoparticles can show quantum confinement effects. Self-healing films can be prepared.

31 Claims, 8 Drawing Sheets

OTHER PUBLICATIONS

Bruchez, Jr., M., et al., "Semiconductor Nanocrystals as Fluorescent Biological Labels", Sicence, vol. 281, pp. 2013-2016 (1998).
Chiappalone, M., et al., "Networks of neurons coupled to microelectrode arrays: a neuronal sensory system for pharmacological applications", *Biosens Bioelectron.*, vol. 18, pp. 627-634 (2003).
Chesnut, J. D., et al., "Selective isolation of transiently transfected cells from a mammalian cell population with vectors expressing a membrane anchored single-chain antibody", *J. Immunol. Methods*, vol. 193, pp. 17-27 (1996).
Chou, W., et al., "Expression of Chimeric Monomer and Dimer Proteins on the Plasma Membrane of Mammalian Cells", *Biotechnol Bioeng*, vol. 65, No. 2, pp. 160-169 (1999).
Coblenz, A., et al., "The role of glutathione biosynthesis in heavy metal resistance in the fission yeast *Schizosaccharomyces pombe*", *FEMS Microbiol. Rev.*, vol. 14, No. 4, pp. 303-308 (1994).
Dameron, C. T., et al., Glutathione-coated Cadmium-Sulfide Crystallites in *Candida glabrata*, vol. 264, No. 29, pp. 17355-17360 (1989).
Dameron, C. T., et al., "Peptide-mediated formation of quantum semiconductors", *Trends Biotechnol.* vol. 8, No. 1, pp. 3-6 (Jan. 1990).
Daugherty, P. S., et al., "Flow cytometric screening of cell-based libraries", *J. Immunol. Methods*, vol. 243, pp. 211-227 (2000).
Feldhaus, M. J., et al., "Flow-cytometric isolation of human antibodies from a nonimmune *Saccharomyces cerevisiae* surface display library", *Nat Biotechnol.* vol. 21, No. 2, pp. 163-170 (Feb. 2003).
Feng, G., et al., "Identification of double-stranded RNA-binding domains in the interferon-induced double-stranded RNA-activated p68 kinase", Proc. Natl. Acad. Sci. USA., vol. 89, pp. 5447-5451 (Jun. 1992).
Flynn, C., et. al., "Synthesis and organization of nanoscale II-VI semiconductor materials using evolved peptide specificity and viral capsid assembly", *J. Mater. Chem.* vol. 13, pp. 2414-2421 (2003).
Flynn, C., et al., "Viruses as vehicles for growth, organization and assembly of materials", Acta Materialia, vol. 51, pp. 5867-5880 (2003) (Advance Article Online).
Gari, E., et al., "A set of vectors with a tetracycline-regulatable promoter system for modulated gene expression in *Saccharomyces cerevisiae*",. Yeast, vol. 13, No. 9, pp. 837-848 (1997).
Georgiou, G., et al., "Display of heterologous proteins on the surface of microorganisms: From the screening of combinatorial libraries to live recombinant vaccines", Nature Biotech., vol. 15, pp. 29-34 (Jan. 1997).
Gossen, M., et al., "Tight control of gene expression in mammalian cells by tetracycline-responsive promoters", *Proc. Natl. Acad. Sci. USA*, vol. 89, pp. 5547-5551 (Jun. 1992).
Hayashi, Y., et al., Unique Properties of Cd-Binding Peptides Induced in Fission Yeast, *Schizosaccharomyces pombe*, Environmental Health Perspectives, vol. 65, pp. 13-19 (1986).
Holler, P. D., et al., "In vitro evolution of a T cell receptor with high affinity for peptide/MHC", *Proc. Natl. Acad. Sci. USA*, vol. 97, no., pp. 5387-5392 (May 9, 2000).
Holmes, J. D., et al., "Cadmium-specific formation of metal sulfide 'Q-particles' by *Klebsiella pneumoniae*", Microbiology, vol. 143, pp. 2521-2530 (1997).
Holmes, J. D., et al., Energy-dispersive X-ray analysis of the extracellular cadmium sulfide crystallites of *Klebsiella aerogenes*, Arch Microbiol., vol. 163, pp. 143-147 (1995).
Holmes, P., et al., "Improved cell line development by a high throughput affinity capture surface display technique to select for high secretors", *J. Immunol. Methods*, vol. 230, pp. 141-147 (1999).
Joho, Masanori, et al., "$Cd^{2+}$ accommodation by *Saccharomyces cerevisiae*", Microbios, vol. 45, pp. 169-179 (1986).
Kieke, M. C., et al., "Selection of functional T cell receptor mutants from a yeast surface-display library", *Proc Natl. Acad. Sci USA.*, vol. 96, No. 10, pp. 5651-5656 (May 11, 1999).
Kuhn, D. M., et al., "Comparison of Biofilms Formed by *Candida albicans* and *Candida parapsilosis* on Bioprosthetic Surfaces", *Infect. Immun.*, vol. 70, No. 2, pp. 878-888 (2002).
Lee, S. W., et al., "Ordering of quantum dots using genetically engineered viruses", *Science* vol. 296, pp. 892-895 (May 3, 2002).

Lin Cereghino, G. P., et al., "Applications of yeast in biotechnology: protein production and genetic analysis", Curr. Opin. Biotechnol., vol. 10, pp. 422-427 (1999).
Mann, S., et al., "Biologically Programmed Nanoparticle Assembly", Adv. Mater., vol. 12, No. 2, pp. 147-150 (2000).
Mann, S., et al., "The Chemistry of Form", Angew. Hem. Int. Ed., vol. 39, pp. 3392-3406 (2000).
Mao, C., et al., "Viral assembly of oriented quantum dot nanowires", *Proc Natl. Acad. Sci* USA, vol. 100, No. 12, pp. 6946-6951 (Jun. 10, 2003).
Mehra, R. K., et al., "Ag(I)-Binding to Phytochelations", J. Inorg. Biochem., vol. 61, pp. 125-142 (1996).
Mehra, R. K., et al., "Role of CdS quantum crystallites in cadmium resistance in *Candida glabrata*", *Biochem Biophys Res Commun.*, vol. 200, No. 3, pp. 1193-1200 (May 16, 1994).
Minney, S. F., et al., "Growth and adaptation of *Saccharomyces cerevisiae* at different cadmium concentrations", *Microbios*, vol. 42, No. 167, pp. 37-44 (1985).
Mutoh, N., et al., "Isolation of mutants of *Schizosaccharomyces pombe* unable to synthesize cadystin, small cadmium-binding peptides", Biochem. Biophys. Res. Commun., vol. 151, No. 1, pp. 32-39 (Feb. 29, 1988).
Naik, R. R., et al., "Biomimetic synthesis and patterning of silver nanoparticles", *Nat Mater*, vol. 1, pp. 169-172 (2002).
No, D., et al., "Ecdysone-inducible gene expression in mammalian cells and transgenic mice", *Proc Natl. Acad. Sci USA*, vol. 93, No. 8, pp. 3346-3351 (1996).
Peelle, B., et al., "Intracellular protein scaffold-mediated display of random peptide libraries for phenotypic screens in mammalian cells", *Chem. Biol.*, vol. 8, pp. 521-534 (2001).
Reese, R. N., et al., "Sulfide stabilization of the cadmium-γ-glutamyl peptide complex of *Schizosaccharomyces pombe*", *J Biol Chem*. vol. 263, No. 26, pp. 12832-12835 (Sep. 15, 1988).
Reynolds, T. B., et al., "Bakers' Yeast, a Model for Fungal Biofilm Formation", *Science*, vol. 291, pp. 878-881 (2001).
Romanos, M. A., et al., "Foreign Gene Expression in Yeast: a Review", Yeast, vol. 8, pp. 423-488 (1992).
Schena, M., et al., "Mammalian Blucocorticoid Receptor Derivatives Enhance Transcription in Yeast", *Science*, vol. 24, pp. 965-967 (1988).
Seeman, N. C., et al., "Emulating biology: building nanostructures from the bottom up", *Proc Natl. Acad. Sci* USA, vol. 99, suppl 2, pp. 6451-6455 (Apr. 30, 2002).
Shusta, E. V., et al. "Increasing the secretory capacity of *Saccharomyces cerevisiae* for production of single-chain antibody fragments", *Nat. Biotech.*, vol. 16, No. 8, pp. 773-777 (Aug. 1998).
Straub, B., et al., "Recombinant maxi-K channels on transistor, a prototype of iono-electronic interfacing", *Nat. Biotechnol* vol. 19, pp. 121-124 (2001).
VanAntwerp J. J., et al., "Fine affinity discrimination by yeast surface display and flow cytometry", *Biotechnol. Prog.*vol. 16, No. 1, pp. 31-37 (Jan.-Feb. 2000).
Wang, S., et al., "Peptides with selective affinity for carbon nanotubes", *Nat. Mater*, vol. 2, pp. 196-200 (2003).
Whaley, S. R., et al., "Selection of peptides with semiconductor binding specificity for directed nanocrystal assembly", *Nature*, vol. 405, pp. 665-668 (Jun. 8, 2000).
Wittrup, K. D., "Disulfide bond formation and eukaryotic secretory productivity", *Curr Opin Biotechnol*. vol. 6, No. 2, pp. 203-208 (Apr. 1995).
Wittrup, K. D., "Protein engineering by cell-surface display", *Curr Opin Biotechnol*, vol. 12, No. 4, pp. 395-395-399, (Aug. 2001).
Wittrup, K. D., "The single cell as a microplate well", *Nat. Biotechnol.*, vol. 18, No. 10, pp. 1039-1040 (Oct. 2000).
Wright, A. P., et al., "Ligand-specific Transactivation of Gene Expression by a Derivative of the Human Glucocorticoid Receptor Expressed in Yeast", *J. Biol. Chem.*, vol. 265, No. 25, pp. 14763-14769 (Sep. 5, 1990).
Wu, X., et al., "Immunofluorescent labeling of cancer marker Her2 and other cellular targets with semiconductor quantum dots", *Nat. Biotechnol.*, vol. 21, pp. 41-46 (2003).

Yeung, Y. A., et al., "Quantitative screening of yeast surface-displayed polypeptide libraries by magnetic bead capture", *Biotechnol Prog.*, vol. 18, No. 2, (Mar.-Apr. 2002).

Peelle et al., "Probing the interface between biomolecules and inorganic materials using yeast surface display and genetic engineering," Acta Biomaterialia, Mar. 2005, 1(2):145-154.

Whaley et al., "Borrowing Ideas from Nature: Peptide Specific Binding to Gallium Arsenide," Materials Research Society Symposium Proceedings, Materials Research Society, 2000, 599:189-199.

US 6,331,391, 12/2001, Wittrup et al. (withdrawn)

* cited by examiner

| Peptide (uM) | 325 | 0 | 32 | 163 | 32 | 325 |
| Salts (uM) | 0 | 1500 | 325 | 325 | 325 | 325 |

CELL DISPLAY LIBRARIES

RELATED APPLICATIONS

This application claims priority to provisional patent application Ser. No. 60/541,757 filed Feb. 5, 2004, "Cell Display Libraries" to Belcher, Peele, et al. which is hereby incorporated by reference and relied upon in its entirety.

STATEMENT OF GOVERNMENT SUPPORT

This invention was made with government support under Grant Nos. CA 101830 and CA96504 awarded by the National Institutes of Health. The government has certain rights in the invention.

BACKGROUND

Combinatorial libraries and "panning" methods are important tools in biotechnology. Despite advances in combinatorial libraries and "panning" methods, however, further advances are needed, particularly advances which provide for commercialization and better versatility. For example, combinatorial libraries which are generated for purposes of research and applications in biotechnology, including immunology and protein chemistry, may not be considered applicable to materials applications. In particular, the fabrication and commercialization of inorganic materials such as, for example, semiconductor, magnetic, or metallic materials are not generally associated with biotechnology or immunology. In general, use of biological self-assembly, specific recognition, and other biomimetic type processes has been limited in the materials arts.

In early efforts, for example, U.S. Pat. No. 5,316,922 to Brown purports to describe methods for identifying and expressing proteins that recognize and adhere to specific probes. See, also, Brown, S., *Proc. Nat'l Acad. Sci.,* 89, 8651 (1992). The work, however, focused on gram-negative bacterial surface display. Other efforts by Belcher et al. have described use of phage display systems for selective recognition against crystalline inorganic surfaces and, more generally, surfaces of technological usefulness. Despite the advantages of phage systems, however, cell systems can provide advantages over phage systems including, for example, the display of relatively large, complex biomolecules at relatively high copy numbers. In addition, growth and expression generally can be better regulated, and cell growth can be more versatile.

SUMMARY

In this section, the invention is merely summarized in a number of different embodiments without limiting the scope of the invention.

In one embodiment, the present invention provides a eukaryotic cell composition comprising a plurality of eukaryotic cells which selectively bind to a solid material having a surface.

In another embodiment, the present invention provides a eukaryotic cell composition consisting essentially of eukaryotic cells which specifically bind to a solid material having a surface and eukaryotic cells which do not specifically bind to the solid material having a surface. The percentage of cells which specifically bind can be sufficiently high, and the percentage of cells which do not specifically bind can be sufficiently low, to commercially exploit the composition for a given application. In a preferred case, the percentage of eukaryotic cells which specifically bind is greater than the percentage of cells which do not specifically bind. For example, the percentage which bind can be more than 60%, or more than 80%.

In another embodiment, the present invention provides a host eukaryotic cell comprising one or more biomolecules which selectively bind with a solid material having a surface.

In another embodiment, the present invention provides a eukaryotic cell which secrets one or more biomolecules which selectively bind with a solid material having a surface.

Still further, the invention also provides an expressed biomolecule composition which selectively binds to a solid material surface, wherein the biomolecule is expressed from a eukaryotic cell.

The invention comprises still further in other embodiments an expressed peptide composition which selectively binds to a solid material surface, wherein the peptide is expressed from a eukaryotic cell.

In another embodiment, the invention provides a cell covered material comprising one or more eukaryotic cells which are selectively bound to a solid material having a surface.

Also provided is an article comprising a solid substrate and one or more eukaryotic cells selectively bound thereto through proteins or peptides on the eukaryotic cell surfaces.

Another embodiment is an article comprising a solid material having a surface and expressed biomolecules from a combinatorial eukaryotic cell display library which are selectively bound to the surface.

In another embodiment is provided a method for selective binding of biomolecules from a cell display library to a solid material surface comprising the steps of:

providing a eukaryotic combinatorial cell display library, wherein the library comprises a plurality of expressed biomolecules, providing a solid material having a surface;

contacting the cell display library with the solid material having a surface under conditions which result in selective binding of the plurality of expressed biomolecules from the eukaryotic cell display library to the surface.

In another aspect, the invention provides a method of growing particulate solid material comprising the steps of:

mixing one or more precursor reagents for the solid particulate material with one or more eukaryotic cell combinatorial display library members selected for specific binding to the solid particulate material, under conditions wherein the solid particulate material is formed in the presence of the one or more eukaryotic combinatorial display library members.

In another embodiment, the invention provides a method of growing particulate solid material comprising the steps of:

identifying a biomolecule which selectively binds to a solid material from a eukaryotic cell display library, mixing one or more precursor reagents for the solid material with the biomolecule under conditions wherein the solid material is formed as a particulate solid material.

The invention also provides a biomolecule which selectively binds to a solid material having a surface and is identified by use of a eukaryotic cell display library including a yeast library. The biomolecules can be peptide or protein.

A basic and novel feature of the invention is to be able to purify and provide biomolecules which can selectively bind, and in some cases specifically bind, to the solid surface. The biomolecules can selectively bind to one structure over another structure when exposed to heterostructures which differ in composition, crystallinity, or both. Compositions can be prepared in which the biomolecules have a desired level of purity with respect to other biomolecules which do not specifically bind. The biomolecules can be free from or attached to a eukaryotic cell scaffold host which, in a preferred embodiment, is yeast. Another feature is that the peptide sequences are generally synthetic or artificial and to the extent known, not natural.

The following are a series of numbered embodiments:

1. A eukaryotic cell composition comprising a plurality of eukaryotic cells which selectively bind to a solid material having a surface.

2. The composition according to 1, wherein the eukaryotic cells are yeast, insect, plant, or mammalian cells.

3. The composition according to 1, wherein the eukaryotic cells are yeast cells.

4. The composition according to 1, wherein the eukaryotic cells comprise biomolecules which selectively bind to a solid material having a surface.

5. The composition according to 1, wherein the eukaryotic cells comprise peptide sequences which selectively bind to a solid material having a surface.

6. The composition according to 1, wherein the solid material having a surface is a crystalline solid material having a surface.

7. The composition according to 1, wherein the solid material having a surface is an inorganic solid material having a surface.

8. The composition according to 1, wherein the solid material having a surface is a semiconductor material having a surface.

9. The composition according to 1, wherein the solid material having a surface is a metallic material having a surface.

10. The composition according to 1, wherein the solid material having a surface is a magnetic material having a surface.

11. The composition according to 1, wherein the solid material having a surface is a ceramic material having a surface.

12. The composition according to 1, wherein the solid material having a surface is an organic material having a surface.

13. The composition according to 1, wherein the solid material having a surface is a polymer material having a surface.

14. The composition according to 1, wherein the solid material having a surface is a crystalline material, an inorganic material, a semiconductor material, a metallic material, a magnetic material, a ceramic material, an organic material, or a polymer material having a surface.

15. The composition according to 1, wherein the eukaryotic cells are yeast, insect, plant, or mammalian cells, and wherein the solid material having a surface is a crystalline material, an inorganic material, a semiconductor material, a metallic material, a magnetic material, a ceramic material, an organic material, or a polymer material having a surface.

16. The composition according to 1, wherein the eukaryotic cells are yeast cells, and wherein the solid material having a surface is a crystalline material, an inorganic material, a semiconductor material, a metallic material, a magnetic material, a ceramic material, an organic material, or a polymer material having a surface.

17. The composition according to 1, wherein the eukaryotic cells are yeast cells, and wherein the solid material having a surface is a semiconductor material, a metallic material, or a magnetic material having a surface.

18. The composition according to 1, wherein the eukaryotic cells are yeast cells, and wherein the solid material having a surface is a semiconductor material having a surface.

19. The composition according to 1, wherein the eukaryotic cells are yeast cells, and wherein the solid material having a surface is a metallic material having a surface.

20. The composition according to 1, wherein the eukaryotic cells are yeast cells, and wherein the solid material having a surface is a magnetic material having a surface.

21. A eukaryotic cell composition consisting essentially of eukaryotic cells which specifically bind to a solid material having a surface and eukaryotic cells which do not specifically bind to the solid material having a surface.

22. The composition according to 21, wherein the eukaryotic cells which specifically bind are yeast, insect, plant, or mammalian cells.

23. The composition according to 21, wherein the eukaryotic cells which specifically bind are yeast cells.

24. The composition according to 21, wherein the eukaryotic cells which specifically bind comprise biomolecules which specifically bind to a solid material having a surface.

25. The composition according to 21, wherein the eukaryotic cells which specifically bind comprise peptide sequences which specifically bind to a solid material having a surface.

26. The composition according to 21, wherein the solid material having a surface is a crystalline solid material having a surface.

27. The composition according to 21, wherein the solid material having a surface is an inorganic solid material having a surface.

28. The composition according to 21, wherein the solid material having a surface is a semiconductor material having a surface.

29. The composition according to 21, wherein the solid material having a surface is a metallic material having a surface.

30. The composition according to 21, wherein the solid material having a surface is a magnetic material having a surface.

31. The composition according to 21, wherein the solid material having a surface is a ceramic material having a surface.

32. The composition according to 21, wherein the solid material having a surface is an organic material having a surface.

33. The composition according to 21, wherein the solid material having a surface is a polymer material having a surface.

34. The composition according to 21, wherein the solid material having a surface is a crystalline material, an inorganic material, a semiconductor material, a metallic material, a magnetic material, a ceramic material, an organic material, or a polymer material having a surface.

35. The composition according to 21, wherein the eukaryotic cells which specifically bind are yeast, insect, plant, or mammalian cells, and wherein the solid material having a surface is a crystalline material, an inorganic material, a semiconductor material, a metallic material, a magnetic material, a ceramic material, an organic material, or a polymer material having a surface.

36. The composition according to 21, wherein the eukaryotic cells which specifically bind are yeast cells, and wherein the solid material having a surface is a crystalline material, an inorganic material, a semiconductor material, a metallic material, a magnetic material, a ceramic material, an organic material, or a polymer material having a surface.

37. The composition according to 21, wherein the eukaryotic cells which specifically bind are yeast cells, and wherein the solid material having a surface is a semiconductor material, a metallic material, or a magnetic material having a surface.

38. The composition according to 21, wherein the eukaryotic cells which specifically bind are yeast cells, and wherein the solid material having a surface is a semiconductor material having a surface.

39. The composition according to 21, wherein the eukaryotic cells which specifically bind are yeast cells, and wherein the solid material having a surface is a metallic material having a surface.

40. The composition according to 21, wherein the eukaryotic cells which specifically bind are yeast cells, and wherein the solid material having a surface is a magnetic material having a surface.

41. A host eukaryotic cell comprising one or more biomolecules which selectively bind with a solid material having a surface.

42. The cell according to 41, wherein the one or more biomolecules comprise peptide or protein.

43. The cell according to 41, wherein the one or more biomolecules comprise human single chain variable fragment antibody displayed as a fusion to Aga2 on yeast.

44. The cell according to 41, wherein the one or more biomolecules comprise peptides displayed as a fusion to Aga2 on yeast.

45. The cell according to 41, wherein the solid material having a surface is an inorganic material.

46. The cell according to 41, wherein the solid material having a surface is an organic material.

47. The cell according to 41, wherein the solid material having a surface is a crystalline material.

48. The cell according to 41, wherein the cell is a mammalian or yeast cell.

49. The cell according to 41, wherein the cell is a yeast cell.

50. The cell according to 41, wherein the cell is a yeast cell and the solid material having a surface is an inorganic material.

51. The cell according to 41, wherein the cell is a yeast cell and the solid material having a surface is an organic material.

52. The cell according to 41, wherein the cell is a yeast cell, the solid material having a surface is an inorganic material, and wherein the one or more biomolecules comprise peptide or protein.

53. The cell according to 41, wherein the cell is a yeast cell, the solid material having a surface is an inorganic material, and wherein the one or more biomolecules comprise human single chain variable fragment antibody displayed as a fusion to Aga2 on yeast.

54. A collection of host cells comprising a plurality of host cells according to 41.

55. A collection of host cells according to 54, wherein the host cells are together with a collection of host eukaryotic cells which do not selectively bind with the solid material having a surface.

56. A eukaryotic cell which secrets one or more biomolecules which selectively bind with a solid material having a surface.

57. The cell according to 56, wherein the cell is a yeast, insect, plant, or mammalian cell.

58. The cell according to 56, wherein the one or more biomolecules are peptide or protein.

59. The cell according to 56, wherein the cell is a yeast cell and the one or more biomolecules are peptide or protein.

60. The cell according to 56, wherein the cell is a yeast cell or a mammalian cell and the one more biomolecules specifically bind to a crystalline solid material having a surface.

61. A cell covered material comprising one or more eukaryotic cells which are selectively bound to a solid material having a surface.

62. The material according to 61, wherein the eukaryotic cells are yeast, insect, plant, or mammalian cells.

63. The material according to 61, wherein the eukaryotic cells are yeast cells.

64. The material according to 61, wherein the eukaryotic cells comprise biomolecules which are selectively bound to a solid material having a surface.

65. The material according to 61, wherein the eukaryotic cells comprise peptide sequences which are selectively bound to a solid material having a surface.

66. The material according to 61, wherein the solid material having a surface is a crystalline solid material having a surface.

67. The material according to 61, wherein the solid material having a surface is an inorganic solid material having a surface.

68. The material according to 61, wherein the solid material having a surface is a semiconductor material having a surface.

69. The material according to 61, wherein the solid material having a surface is a metallic material having a surface.

70. The material according to 61, wherein the solid material having a surface is a magnetic material having a surface.

71. The material according to 61, wherein the solid material having a surface is a ceramic material having a surface.

72. The material according to 61, wherein the solid material having a surface is an organic material having a surface.

73. The material according to 61, wherein the solid material having a surface is a polymer material having a surface.

74. The material according to 61, wherein the solid material having a surface is a crystalline material, an inorganic material, a semiconductor material, a metallic material, a magnetic material, a ceramic material, an organic material, or a polymer material having a surface.

75. The material according to 61, wherein the eukaryotic cells are yeast, insect, plant, or mammalian cells, and wherein the solid material having a surface is a crystalline material, an inorganic material, a semiconductor material, a metallic material, a magnetic material, a ceramic material, an organic material, or a polymer material having a surface.

76. The material according to 61, wherein the eukaryotic cells are yeast cells, and wherein the solid material having a surface is a crystalline material, an inorganic material, a semiconductor material, a metallic material, a magnetic material, a ceramic material, an organic material, or a polymer material having a surface.

77. The material according to 61, wherein the eukaryotic cells are yeast cells, and wherein the solid material having a surface is a semiconductor material, a metallic material, or a magnetic material having a surface.

78. The material according to 61, wherein the eukaryotic cells are yeast cells, and wherein the solid material having a surface is a semiconductor material having a surface.

79. The material according to 61, wherein the eukaryotic cells are yeast cells, and wherein the solid material having a surface is a metallic material having a surface.

80. The material according to 61, wherein the eukaryotic cells are yeast cells, and wherein the solid material having a surface is a magnetic material having a surface.

81. The material according to 61, wherein the solid material having a surface is a nanoparticulate material.

82. The material according to 61, wherein the solid material having a surface is a nanoparticulate material and is also a crystalline material, an inorganic material, a semiconductor material, a metallic material, a magnetic material, a ceramic material, an organic material, or a polymer material having a surface.

83. The material according to 61, wherein the solid material having a surface is a nanoparticulate material and is also a semiconductor material, a metallic material, or a magnetic material having a surface.

84. The material according to 61, wherein the solid material having a surface is a nanoparticulate material and is also a semiconductor material having a surface.

85. The material according to 61, wherein the solid material having a surface is a nanoparticulate material and is also a metallic material having a surface.

86. The material according to 61, wherein the solid material having a surface is a nanoparticulates material and is also a magnetic material having a surface.

87. The material according to 61, wherein the cell-covered material is a self-healing cell-covered material.

88. An article comprising a solid substrate and one or more eukaryotic cells selectively bound thereto through proteins or peptides on the eukaryotic cell surfaces.

89. The article according to 88, wherein the solid substrate is an electrode and the eukaryotic cells are human cells.

90. The article according to 88, wherein the solid substrate is an inorganic material and the eukaryotic cells are mammalian cells.

91. An article comprising a solid material having a surface and expressed biomolecules from a combinatorial eukaryotic cell display library which are selectively bound to the surface.

92. The article of 91, wherein the cell display library is a yeast, insect, plant, or mammalian cell display library.

93. The article of 91, wherein the cell display library is a yeast cell display library or a mammalian cell display library.

94. The article of 91, wherein the cell display library is a yeast cell display library.

95. The article of 91, wherein the cell display library is a human cell display library.

96. The article of 91, wherein the cell display library is a mammalian cell display library.

97. The article of 91, wherein the expressed biomolecules are secreted.

98. The article of 91, wherein the expressed biomolecules are surface displayed on the eukaryotic cell.

99. The article according to 91, wherein the combinatorial cell display library is a human single chain variable fragment antibody library displayed as a fusion on yeast.

100. The article according to 91, wherein the biomolecules are proteins or peptides.

101. The article according to 91, wherein the cell display library comprises members having surfaces comprising expressed biomolecules of polypeptide binding sites which result in the selective binding.

102. The article of 91, wherein the expressed biomolecules comprise polypeptide binding sites which result in the selective binding.

103. The article according to 91, wherein the solid material substrate having a surface is a crystalline solid material having a surface.

104. The article according to 91, wherein the solid material substrate having a surface is an inorganic solid material having a surface.

105. The article according to 91, wherein the solid material having a surface is a semiconductor material having a surface.

106. The article according to 91, wherein the solid material having a surface is a metallic material having a surface.

107. The article according to 91, wherein the solid material having a surface is a magnetic material having a surface.

108. The article according to 91, wherein the solid material having a surface is a ceramic material having a surface.

109. The article according to 91, wherein the solid material having a surface is an organic material having a surface.

110. The article according to 91, wherein the solid material having a surface is a single crystalline, non-particulate solid material.

111. The article according to 91, wherein the solid material having a surface is a particulate, crystalline solid material.

112. The article according to 91, wherein the solid material having a surface is a microparticulate material.

113. The article according to 91, wherein the solid material having a surface is a nanoparticulate material.

114. The article according to 91, wherein the solid material having a surface is surface treated to limit non-specific interactions between the expressed biomolecules and the surface.

115. The article according to 91, wherein the biomolecules are genetically engineered for specific binding to a different surface.

116. The article according to 91, wherein the cell display library is a yeast cell display library, and wherein the solid material having a surface is a single crystalline, non-particulate solid material.

117. The article according to 91, wherein the cell display library is a yeast cell display library, and wherein the solid material substrate having a surface is an inorganic solid material having a surface.

118. The article according to 91, wherein the cell display library is a yeast cell display library, wherein the solid material substrate having a surface is an inorganic or organic solid material having a surface.

119. The article according to 91, wherein the cell display library is a yeast cell display library, and wherein the solid material substrate having a surface is an inorganic or organic crystalline solid material having a surface.

120. An article comprising a solid material having a surface and one or more biomolecules selectively bound to the surface, wherein the one or more biomolecules are synthetic peptides or proteins which have a sequence obtained from a combinatorial eukaryotic cell display library.

121. A method for selective binding of biomolecules from a cell display library to a solid material surface comprising the steps of:
providing a eukaryotic combinatorial cell display library, wherein the library comprises a plurality of expressed biomolecules,
providing a solid material having a surface;
contacting the cell display library with the solid material having a surface under conditions which result in selective binding of the plurality of expressed biomolecules from the eukaryotic cell display library to the surface.

122. The method of 121, wherein the combinatorial cell display library is a yeast, insect, plant, or mammalian cell display library.

123. The method according to 121, wherein the combinatorial cell display library is a yeast library.

124. The method according to 121, wherein the combinatorial cell display library is a human single chain variable fragment antibody library displayed as a fusion on yeast.

125. The method according to 121, wherein the combinatorial cell display library is a peptide library displayed as a fusion on yeast.

126. The method according to 121, wherein the plurality of biomolecules is a plurality of proteins or peptides.

127. The method according to 121, wherein the cell display library comprises members having surfaces comprising expressed biomolecules of polypeptide binding sites which result in the selective binding.

128. The method according to 121, wherein the solid material having a surface is a crystalline solid material having a surface.

129. The method according to 121, wherein the solid material having a surface is an inorganic solid material having a surface.

130. The method according to 121, wherein the solid material having a surface is a semiconductor material having a surface.

131. The method according to 121, wherein the solid material having a surface is a metallic material having a surface.

132. The method according to 121, wherein the solid material having a surface is a magnetic material having a surface.

133. The method according to 121, wherein the solid material having a surface is a ceramic material having a surface.

134. The method according to 121, wherein the solid material having a surface is an organic material having a surface.

135. The method according to 121, wherein the solid material having a surface is a polymer material having a surface.

136. The method according to 121, wherein the solid material having a surface is surface treated before the contacting step to limit non-specific interactions between the plurality of expressed biomolecules and the surface.

137. The method according to 121, wherein the solid material having a surface is a single crystalline, non-particulate solid material.

138. The method according to 121, wherein the solid material having a surface is a particulate solid material.

139. The method according to 121, further comprising the step of regulating the expression of the library.

140. The method according to 121, further comprising the step of isolating expressed biomolecules which selectively bind to the solid material having a surface.

141. The method according to 121, wherein the combinatorial cell display library is a yeast library, and wherein the solid material having a surface is an inorganic solid material having a surface.

142. The method according to 121, wherein the combinatorial cell display library is a yeast library, wherein the solid material having a surface is an inorganic solid material having a surface, and wherein the cell display library comprises yeast members having surfaces comprising expressed biomolecules of polypeptide binding sites which result in the selective binding.

143. The method according to 121, wherein the combinatorial cell display library is a yeast library, wherein the solid material having a surface is an inorganic solid material having a surface, wherein the cell display library comprises yeast members having surfaces comprising expressed biomolecules of polypeptide binding sites which result in the selective binding, and wherein the solid material having a surface is surface treated to limit non-specific interactions between the plurality of expressed biomolecules and the surface.

144. The method according to 121, wherein the combinatorial cell display library is a yeast library, wherein the solid material having a surface is an organic solid material having a surface, wherein the cell display library comprises members having surfaces comprising expressed biomolecules of polypeptide binding sites which result in the selective binding, and wherein the solid material having a surface is surface treated to limit non-specific interactions between the plurality of expressed biomolecules and the surface.

145. A method of growing particulate solid material comprising the steps of: mixing one or more precursor reagents for the solid particulate material with one or more eukaryotic cell combinatorial display library members selected for specific binding to the solid particulate material, under conditions wherein the solid particulate material is formed in the presence of the one or more eukaryotic combinatorial display library members.

146. The method according to 145, wherein the solid particulate material is nanoparticulate material.

147. The method according to 145, wherein the solid particulate material is inorganic particulate material.

148. The method according to 145, wherein the solid particulate material is organic particulate material.

149. The method according to 145, wherein the solid particulate material is magnetic particulate material.

150. The method according to 145, wherein the solid particulate material is metallic particulate material.

151. The method according to 145, wherein the solid particulate material is nanocrystalline material.

152. The method according to 145, wherein the solid particulate material is a quantum dot material.

153. The method according to 145, wherein the solid particulate material is a semiconductor material.

154. The method according to 145, wherein the conditions include temperature of about 300° C. or less.

155. The method according to 145, wherein the conditions include temperature of about 100° C. or less.

156. The method according to 145, wherein the conditions include temperature of about 0° C. to about 40° C.

157. The method according to 145, wherein the conditions include temperature of about 20° C. to about 40° C.

158. A method of growing particulate solid material comprising the steps of:
identifying a biomolecule which selectively binds to a solid material from a eukaryotic cell display library,
mixing one or more precursor reagents for the solid material with the biomolecule under conditions wherein the solid material is formed as a particulate solid material.

159. The method according to 158, wherein the eukaryotic cell display library is a yeast or mammalian cell display library.

160. The method according to 158, wherein the eukaryotic cell display library is a yeast cell display library.

161. The method according to 158, wherein the biomolecule is a peptide or protein.

162. The method according to 158, wherein the biomolecule is an antibody.

163. The method according to 158, wherein the solid material is a crystalline material.

164. The method according to 158, wherein the solid material is an inorganic material.

165. The method according to 158, wherein the solid material is a semiconductor material.

166. The method according to 158, wherein the particulate solid material is a nanoparticulate solid material.

167. The method according to 158, wherein the eukaryotic cell display library is a yeast cell display library, wherein the biomolecule is a peptide or protein, and wherein the solid material is a crystalline material.

168. The method according to 158, wherein the eukaryotic cell display library is a yeast cell display library, wherein the biomolecule is a peptide or protein, wherein the solid material is an inorganic material, and wherein the particulate solid material is a nanoparticulate solid material.

169. The method of 168, wherein the nanoparticulate solid material has an average particle diameter of about 1 nm to about 10 nm.

170. An expressed biomolecule composition which selectively binds to a solid material surface, wherein the biomolecule is expressed from a eukaryotic cell.

171. The biomolecule of 170, wherein the eukaryotic cell is a yeast, insect, plant, or mammalian cell, and the biomolecule is a peptide or protein.

172. The biomolecule of 170, wherein the eukaryotic cell is a yeast, insect, plant, or mammalian cell, and the biomolecule is an antibody.

173. The biomolecule of 170, wherein the eukaryotic cell is a yeast cell and the biomolecules is a peptide or protein.

174. The biomolecule according to 170, wherein the eukaryotic cell surface displays the biomolecule.

175. The biomolecule according to 170, wherein the eukaryotic cell secretes the biomolecule.

176. An expressed peptide composition which selectively binds to a solid material surface, wherein the peptide is expressed from a eukaryotic cell.

177. The peptide of 176, wherein the eukaryotic cell is a yeast cell.

178. The peptide according to 176, wherein the eukaryotic cell surface displays the peptide.

179. The peptide according to 176, wherein the eukaryotic cell surface secretes the peptide.

180. A biomolecule which selectively binds to a solid material having a surface and is identified by use of a eukaryotic cell display library.

181. The biomolecule according to 180, wherein the eukaryotic cell display library is a yeast library.

182. The biomolecule according to 180, wherein the biomolecule is a peptide or protein.

183. The biomolecule according to 181, wherein the biomolecule is a peptide or protein.

DETAILED DESCRIPTION

I. Introduction and Technical Literature

Figure 1:
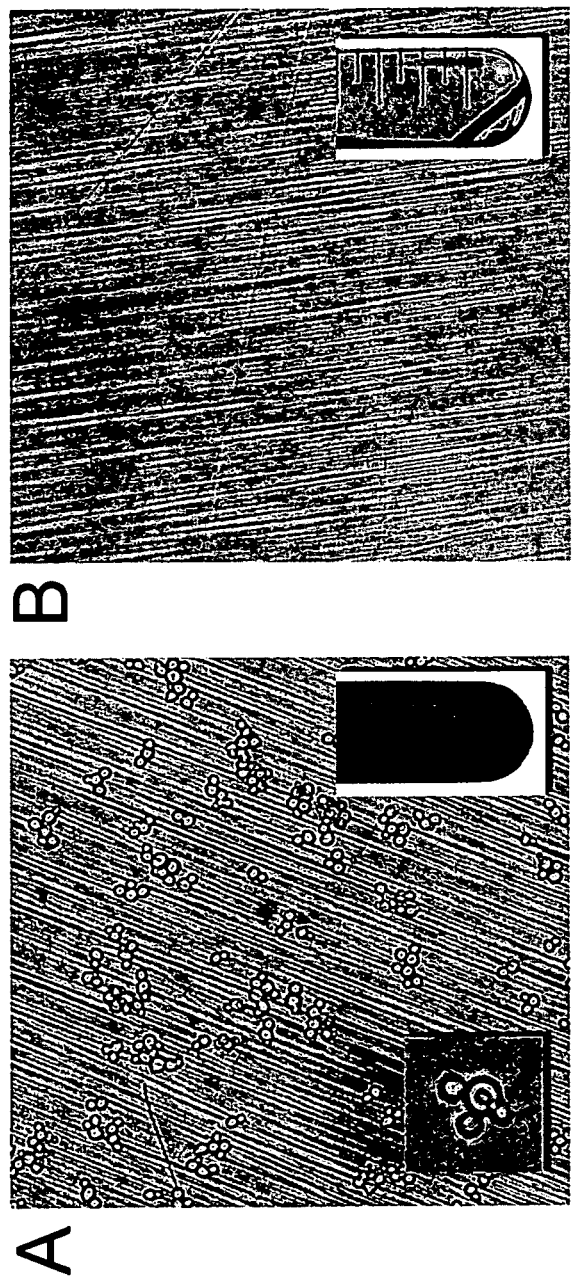
FIG. 1. Yeast library bound to CdS. (A) Yeast library expressing surface-displayed scFv antibodies bound to single crystal CdS [A-plate] after panning round d3. (B) A yeast control clone expressing CD20 ectodomain in place of the scFv library does not bind single crystal CdS. Transmission light microscopy images were ca. 260 $\mu m^2$ in size. Insets show a single budding yeast cell bound to CdS, and yeast cultures 24 h after the corresponding CdS crystals were incubated in SD.

In describing the invention, the applicants refer to technical literature which can be used in the practice of the invention, but no admission is made that the cited technical literature is prior art. In addition to the literature noted in this introduction, a list of references is also provided at the end of the specification. These references are hereby incorporated by reference in their entirety.

Provisional patent application Ser. No. 60/541,757 filed Feb. 5, 2004, "Cell Display Libraries" to Belcher, Peele, et al.

is hereby incorporated by reference and relied upon in its entirety including figures, tables, claims, and working examples.

In the present invention, screening of eukaryotic combinatorial cell display libraries, including combinatorial yeast cell display libraries, can be useful for generating protein-specific affinity reagents for therapeutics and drug discovery (1). These libraries can comprise a plurality of expressed biomolecules. Although many advances have been made with yeast display systems (2), yeast display libraries have not been screened against solid materials having a surface including, for example, inorganic materials and other technologically important materials as described in the present invention. Recently, there have been useful developments in developing protein specificity for inorganic materials with the idea of being able to select or evolve proteins to bind to and or direct the synthesis of various types of inorganic materials (3). Examples include phage displayed peptide libraries (4-8), bacterial surface displayed polypeptides (9-11) and monoclonal antibody libraries (12). Although these systems have been useful, eukaryotic and yeast displayed libraries present certain advantages, described further herein.

In the present invention, combinatorial protein diversity displayed on eukaryotic cells can be utilized to combine both the recognition capabilities of protein-based systems for inorganic materials and the power of genetics with the genetic regulation, growth, and sensory capabilities of a eukaryotic cell. Eukaryotic cells such as yeast are able to efficiently display post-translationally modified or complex proteins such as antibody fragments (13) and receptors (14), not as readily achieved using bacterial or phage display systems. Further, advantages of using cells for screening are the potential for high copy number display, ease of detection by light microscopy or fluorescence-activated cell sorting (FACS), amplification without using a secondary host, and the ability to genetically regulate display (15, 16). The relatively massive cell in comparison to phage allows for the application of mechanical forces to the particle-like cell body to quantitatively probe the biomolecular-material interaction (17). An additional advantage of using yeast over other cell or protein based systems for potential production of biomolecular templated materials is the scalability and cost efficiency of yeast, which has been explored and utilized for centuries (18).

A new method for identifying protein biomolecules that interact with inorganic materials is described herein, that relies on, in some embodiments, living yeast cells to express and display on their surface a combinatorial library of proteins or peptides, which are then panned against a material, and subsequently the bound cells are amplified. For example, a human single chain antibody library displayed on *Saccharomyces cerevisiae* (13) can be panned against a diverse collection of technologically important materials, including semiconductor, magnetic, and metallic materials. Material-specific antibodies and polypeptides can be identified, and general characteristics of the system are described. In particular, peptide sequences resulting from frame-shifts and truncations can be preferentially isolated over fill-length single chain antibodies, despite their minority representation in the starting population. This new system provides a route for finding medically or industrially applicable cell or protein-based reagents that mediate interactions with technologically important materials, microelectronics, or hybrid devices. In addition, because organisms have evolved intricate systems to control inorganic materials as evident in biomineralization (19-21), being able to do selections at a cellular level with an engineered system can provide insights into molecular mechanisms of natural biomineralization systems.

Using the methods of the present invention, biomolecules can be identified from cell display libraries which are capable of binding, growing, assembling, and organizing materials of technological interest. The identification can be carried out by screening processes, wherein for example the libraries can be repetitively contacted with solid materials having a surface, and those library members which selectively bind to the surface are progressively isolated and enriched over those which do not bind to the surface with repetitive screening. These methods for selective enrichment can be called panning or biopanning.

For example, screening methods with selective enrichment are known: phage display combinatorial screening methods against solid surfaces have been described in and can be referred to in the practice of the present invention including, for example, U.S. patent publications to Belcher et al.: (1) "Biological Control of Nanoparticle Nucleation, Shape, and Crystal Phase"; 2003/0068900 published Apr. 10, 2003; (2) "Nanoscale Ordering of Hybrid Materials Using Genetically Engineered Mesoscale Virus"; 2003/0073104 published Apr. 17, 2003; (3) "Biological Control of Nanoparticles"; 2003/0113714 published Jun. 19, 2003; and (4) "Molecular Recognition of Materials"; 2003/0148380 published Aug. 7, 2003, all of which are incorporated by reference in their entirety.

Additional U.S. patent applications to Belcher et al. include (5) Ser. No. 10/654,623 filed Sep. 4, 2003 ("Composition, Method, and Use of BiFunctional Biomaterials"); (6) Ser. No. 10/665,721, filed Sep. 22, 2003 ("Peptide Mediated Synthesis of Metallic and Magnetic Nanoparticles"); (7) Ser. No. 10/668,600 filed Sep. 24, 2003 ("Fabricated Biofilm Storage Device"); (8) U.S. Provisional Ser. No. 60/510,862 ("Viral Fibers") filed Oct. 15, 2003 and U.S. regular application Ser. No. 10/965,665 filed Oct. 15, 2004; (9) U.S. Provisional Ser. No. 60/511,102 ("Multifunctional Biomaterials . . . ") filed Oct. 15, 2003 and U.S. regular application Ser. No. 10/965,227 filed Oct. 15, 2004; and (10) U.S. Provisional Ser. No. 60/534,102 ("Inorganic Nanowires") filed Jan. 5, 2004 and U.S. regular application Ser. No. (currently unassigned) filed Oct. 29, 2004.

Additional technical literature to Belcher et al which can be useful for practice of the present invention including identification of biomolecules and binding with different types of materials include:

Mao C, et al. Viral assembly of oriented quantum dot nanowires. *Proc Natl Acad Sci* USA. Jun. 10, 2003; 100(12):6946-51.

Lee S W, et al. Ordering of quantum dots using genetically engineered viruses. *Science*. May 3, 2002; 296(5569): 892-5.

Flynn C, et. al. Synthesis and organization of nanoscale II-VI semiconductor materials using evolved peptide specificity and viral capsid assembly. *J. Mater. Chem.* 2003, 13 (Advance Article Online)

Seeman N C, Belcher A M. Emulating biology: building nanostructures from the bottom up. *Proc Natl Acad Sci* USA. Apr. 30, 2002; 99 Suppl 2:6451-5.

Whaley et al. Selection of peptides with semiconductor binding specificity for directed nanocrystal assembly. *Nature*. Jun. 8, 2000; 405(6787):665-8.

In addition, yeast display libraries are described in, for example, U.S. Pat. No. 6,300,065 to Kieke et al. (Oct. 9, 2001); U.S. Pat. No. 6,331,391 to Wittrup et al. (Dec. 18, 2001; withdrawn); U.S. Pat. Nos. 6,423,538; 6,300,065; and patent application Publication 2002/0058253 to Kranz et al.

(May 16, 2002). Additional technical literature by Wittrup et al. can be used in the practice of the present invention including, for example:

- Bhatia et al. Rolling Adhesion Kinematics of Yeast Engineered To Express Selectins. *Biotechnol Prog*. Jun. 6, 2003; 19(3):1033-1037.
- Feldhaus et al. Flow-cytometric isolation of human antibodies from a nonimmune *Saccharomyces cerevisiae* surface display library. *Nat Biotechnol*. February 2003; 21(2):163-70.
- Yeung Y A, Wittrup K D. Quantitative screening of yeast surface-displayed polypeptide libraries by magnetic bead capture. *Biotechnol Prog*. March-April 2002; 18(2):212-20.
- Wittrup K D. Protein engineering by cell-surface display. *Curr Opin Biotechnol*. August 2001; 12(4):395-9.
- Boder E T, Wittrup K D. Yeast surface display for directed evolution of protein expression, affinity, and stability. *Methods Enzymol*. 2000; 328:430-44.
- Wittrup K D. The single cell as a microplate well. *Nat Biotechnol*. October 2000; 18(10):1039-40.
- Boder E T, Midelfort K S, Wittrup K D. Directed evolution of antibody fragments with monovalent femtomolar antigen-binding affinity. *Proc Natl Acad Sci USA*. Sep. 26, 2000; 97(20):10701-5.
- Boder E T, Wittrup K D. Optimal screening of surface-displayed polypeptide libraries. *Biotechnol Prog*. January-February 1998; 14(1):55-62.
- Holler P D, et al. In vitro evolution of a T cell receptor with high affinity for peptide/MHC. *Proc Natl Acad Sci USA*. May 9, 2000; 97(10):5387-92.
- Bannister S J, Wittrup K D. Glutathione excretion in response to heterologous protein secretion in *Saccharomyces cerevisiae*. *Biotechnol Bioeng*. May 20, 2000; 68(4):389-95.
- VanAntwerp J J, Wittrup K D. Fine affinity discrimination by yeast surface display and flow cytometry. *Biotechnol Prog*. January-February 2000; 16(1):31-7.
- Kieke M C, et al. Selection of functional T cell receptor mutants from a yeast surface-display library. *Proc Natl Acad Sci USA*. May 11, 1999; 96(10):5651-6.
- Shusta E V, et al. Increasing the secretory capacity of *Saccharomyces cerevisiae* for production of single-chain antibody fragments. *Nat Biotech*. 1998 August 1998; 16(8):773-7.
- Boder E T, Wittrup K D. Yeast surface display for screening combinatorial polypeptide libraries. *Nat Biotechnol*. June 1997; 15(6):553-7.

See also: Wittrup K D. Disulfide bond formation and eukaryotic secretory productivity. Curr Opin Biotechnol. April 1995; 6(2):203-8. Wittrup K D. Disulfide bond formation and eukaryotic secretory productivity. *Curr Opin Biotechnol*. April 1995; 6(2):203-8.

Additional references which can be used in the practice of the present invention can be found in the list of references at the end of the specification.

In practicing the present invention, molecular biology, genetic engineering, microbiology, and recombinant DNA techniques within the skill of the art can be used, and such techniques are fully explained in the literature (e.g., see, for example, U.S. Pat. Nos. 6,423,538; 6,331,391 (withdrawn); and U.S. Pat. No. 6,300,065 and references cited in U.S. Pat. No. 6,331,391 to Wittrup et al. at col. 9, line 60 through col. 10, line 6; and references cited at end of this specification). See also U.S. Pat. No. 5,866,344 to Georgiou; U.S. Pat. No. 5,935,823 to Fowlkes et al; and U.S. Pat. No. 6,214,613 to Higuchi et al.

Finally, one embodiment of the present invention is a yeast system and the following references can be used is providing yeast systems according to the invention which interact with solid material surfaces:

- Joho M, Yamanaka C, Murayama T. Cd2+ accommodation by *Saccharomyces cerevisiae*. *Microbios*. 1986; 45(184-185):169-79.
- Dameron C T, Winge D R. Peptide-mediated formation of quantum semiconductors. *Trends Biotechnol*. January 1990; 8(1):3-6.
- Dameron C T, Smith B R, Winge D R. Glutathione-coated cadmium-sulfide crystallites in *Candida glabrata*. *J Biol Chem*. Oct. 15, 1989; 264(29):17355-60.
- Mutoh N, Hayashi Y. Isolation of mutants of *Schizosaccharomyces pombe* unable to synthesize cadystin, small cadmium-binding peptides. *Biochem Biophys Res Commun*. Feb. 29, 1988; 151(1):32-9.
- Hayashi Y, Nakagawa C W, Murasugi A. Unique properties of Cd-binding peptides induced in fission yeast, *Schizosaccharomyces pombe*. *Environ Health Perspect*. March 1986; 65:13-9.
- Barbas J, Santhanagopalan V, Blaszczynski M, Ellis W R Jr, Winge D R. Conversion in the peptides coating cadmium:sulfide crystallites in *Candida glabrata*. *J Inorg Biochem*. Nov. 1, 1992; 48(2):95-105.
- Mehra R K, Mulchandani P, Hunter T C. Role of CdS quantum crystallites in cadmium resistance in *Candida glabrata*. *Biochem Biophys Res Commun*. May 16, 1994; 200(3):1193-200.
- Holmes J D, Smith P R, Evans-Gowing R, Richardson D J, Russell D A, Sodeau J R. Energy-dispersive X-ray analysis of the extracellular cadmium sulfide crystallites of *Klebsiella aerogenes*. *Arch Microbiol*. February 1995; 163(2):143-7.
- Reese R N, Winge D R. Sulfide stabilization of the cadmium-gamma-glutamyl peptide complex of *Schizosaccharomyces pombe*. *J Biol Chem*. Sep. 15, 1988; 263(26):12832-5
- Holmes J D, Richardson D J, Saed S, Evans-Gowing R, Russell D A, Sodeau J R. Cadmium-specific formation of metal sulfide 'Q-particles' by *Klebsiella pneumoniae*. *Microbiology*. August 1997; 143 (Pt 8):2521-30.
- Mehra R K, Tran K, Scott G W, Mulchandani P, Saini S S. Ag(I)-binding to phytochelatins. *J Inorg Biochem*. February 1996; 61(2):125-42.
- Coblenz A, Wolf K. The role of glutathione biosynthesis in heavy metal resistance in the fission yeast *Schizosaccharomyces pombe*. *FEMS Microbiol Rev*. August 1994 August; 14(4):303.
- Mehra R K, Mulchandani P, Hunter T C. Role of CdS quantum crystallites in cadmium resistance in *Candida glabrata*. *Biochem Biophys Res Commun*. May 16, 1994; 200(3):1193-200.
- Mehra R K, Mulchandani P, Hunter T C. Role of CdS quantum crystallites in cadmium resistance in *Candida glabrata*. *Biochem Biophys Res Commun*. May 16, 1994; 200(3):1193-200.
- Minney S F, Quirk A V. Growth and adaptation of *Saccharomyces cerevisiae* at different cadmium concentrations. *Microbios*. 1985; 42(167):37-44.

II. Cell Display Library

Cell display combinatorial libraries are known in the art (see, for example, section I above; see reference 2 below and references cited therein; see also, for example, U.S. Pat. No. 6,214,613 to K. Higuchi et al. "Expression Screening Vector"). For example, the display of proteins on cell surfaces can provide a support, similar to the immobilization of a protein on, for example, sepharose. Rather than covalently link a soluble protein to an inert support matrix, an expressed protein can be displayed on a cell surface. Then, the cells can be handled as if they were micron-sized beads of support media. Hence, cell surface display can be used to circumvent separate expression, purification, and immobilization of binding proteins and enzymes. In addition, the biomolecules can be secreted from the cell rather than displayed on the surface.

Eukaryotic combinatorial cell display libraries can be used in the practice of the present invention, including yeast libraries, wherein the library comprises a plurality of expressed biomolecules. Eukaryotic cell display libraries include, for example, yeast, insect, plant, and mammalian libraries. Cells can be in a cell line or can be a primary culture cell type.

Mammalian cells are known including their genetic engineering and cell surface display procedures. See, for example, U.S. Pat. No. 6,255,071 to Beach et al. (Jul. 3, 2001); U.S. Pat. No. 6,207,371 to Zambrowicz et al. (Mar. 27, 2001); and U.S. Pat. No. 6,136,566 to Sands et al. (Oct. 24, 2000). See also, for example, Holmes et al., *J. Immunol. Methods,* 1999, 230: 141-147; Chesnut et al. *J. Immunol. Methods,* 1996, 193: 17-27; Chou et al., *Biotechnol Bioeng,* 1999, 65: 160-169.

In particular, yeast libraries are preferred in this invention. The selection of the yeast is not particularly limited. For example, the yeast, *Saccharomyces cerevisiae*, (*S. cerevisiae*) can be used.

The general cellular characteristics of yeast are known and can be used in the practice of the present invention. See, for example, Walker, G. M. *Yeast Physiology and Biotechnology,* John Wiley, 1998. For example, yeasts of different cell size, shape, and color can be used, and the physical and chemical conditions of the yeast environment can be altered to alter the yeast as desired. An example of yeast cells is provided in the Working Examples below. *S. cerevisiae* can be generally ellipsoidal in shape ranging from, for example, about 5 microns to about 10 microns at the large diameter and about one micron to about 7 microns at the small diameter. The mean cell volume can be, for example, about 25 cubic microns to about 35 cubic microns for a haploid cell. The mean cell volume can be, for example, about 50 cubic microns to about 60 cubic microns for a diploid cell. The cell size can increase with age. The yeast can comprise macromolecular constituents including, for example, proteins, glycoproteins, polysaccharides, polyphosphates, lipids, and nucleic acids. Known cytology methods can be used including microscopy, phase-contrast microscopy, staining methods, fluorochromic dyes, fluorescence microscopy, green fluorescent proteins (GFP), and flow cytometry.

The expressed biomolecules can be genetically encoded biomolecules that provide interactions upon which specific and selective binding can be achieved in surface interactions with solid materials. For example, the biomolecules can be encoded in a plasmid, and the library produced in or on the surface of, or secreted from yeast cells. In another example, the biomolecules can be genetically encoded in a retroviral construct, and the library can be produced in or on the surface of cells such as, for example, mammalian or human cells.

Biomolecules are not particularly limited but generally can be the subect of cellular expression processes. Biomolecules can include peptides, oligopeptides, and polypeptides. They can be proteins. They can be antibodies or fragments of antibodies. Modifications of biomolecules can include biotinylation, glycosylation, disulfide formation, glycosylation, proteolysis, myristylation, prenelation, palmitylation, farnesylation, ligation, incorporation of non-natural amino acids, cyclization, and incorporation of ions.

The biomolecules can comprise peptides and proteins and derivatives thereof. The biomolecules can comprise antibodies or antibody fragments, including scFv fragments. The type of interaction between the biomolecule and the surface is not particularly limited so long as binding can be achieved but interactions known in the art include electrostatic, ionic, hydrophobic, van der waals, covalent, adhesion, and the like.

The biomolecules can be produced within cells or on the surface of cells. In one embodiment, the cell display library is a human single chain variable fragment antibody library displayed on the surface of a yeast.

In one embodiment, the plurality of biomolecules is a plurality of proteins or peptides. In particular, the cell display library can comprise members having surfaces comprising expressed biomolecules with binding sites such as polypeptide binding sites which result in the selective binding.

In one embodiment, the biomolecules can be genetically engineered for specific binding to a different surface in addition to the solid material having a surface. The biomolecule can, for example, have two or more sites which provide for selective or specific binding, functioning as a linker moiety. For example, the biomolecule can be bound to the solid material having a surface and then bound to an additional surface at the second binding site.

The library diversity is not particularly limited but can be, for example, greater than $10^4$, greater than $10^5$, greater than $10^6$, greater than $10^7$, or greater than $10^8$ clones. Screening with a single library can be carried out. Alternatively, screening with a series of smaller libraries can be also carried out.

An important aspect of the invention is further control of the process by regulatable systems including temporal or spatial controls. For example, the display of the biomolecule can be regulated by control of transcription or translation of the biomolecule. External cues can be used which provide many options for additional control including temporal control over cell growth, signal transduction, transcription, translation, and protein function. In one embodiment, for example, a biomolecule such as a peptide can be encoded downstream of a nutritionally regulatable genetic element, such as galactose regulatable promoter. In this embodiment, switching the host cell into growth media containing either glucose or galactose controls transcription of the peptide. Hence, nutrition can be used to regulate the expression of the library. Regulation of display or secretion of the peptide can enable temporal or spatial control over material deposition if the encoded peptide can bind or assemble nanocrystalline or other materials. Temporal control can be accomplished by an external cue or stimulus that affects a signal transduction pathway, transcription, translation, or intramolecular interactions. Regulation can be controlled by a variety of different types of switching mechanisms. These mechanisms can directly affect the transcription, translation, folding, stability, or processing of the biomolecules, or induce the switch mechanism through a signal transduction pathway. Switching mechanisms are known in the art. The display of biomolecules can be temporally controlled by external cues including, but not limited to, a small molecule, a diffusible ligand such as, for example, a growth factor, a cytokine, a pheromone, a hormone, a neurotransmitter, a sugar, an amino acid, a nucleotide, nutritional compounds, light, radiofrequency, mechanotransduction, magnetic field, electric field, current, temperature, and the like.

Examples of regulatable systems include:
1. Gossen, M. and Bujard, H. (1992). Tight control of gene expression in mammalian cells by tetracycline-responsive promoters. *Proc Natl Acad Sci USA* 89, 5547-51.
2. Gari E, Piedrafita L, Aldea M, Herrero E. A set of vectors with a tetracycline-regulatable promoter system for modulated gene expression in *Saccharomyces cerevisiae. Yeast.* July 1997; 13(9):837-48.
3. No, D., Yao, T. P. and Evans, R. M. (1996) *Proc Natl Acad Sci USA* 93(8):3346-51. (the insect hormone ecdysone or its analog ponasterone A (pona) can activate transcription in mammalian cells harboring both the gene for the *Drosophila melanogaster* ecdysone receptor and a promoter containing a binding site for the ecdysone receptor.)

In addition, different promoters can be used in yeast expression. For example, the Gal 1,10 promoter is inducible by galactose. The regulatory region containing the UAS sequences can be placed upstream of any other gene to confer galactose inducible expression and glucose repression. The ADH2 promoter is glucose repressible and it is strongly transcribed on non-fermentable carbon sources (similar to GAL 1,10 except not inducible by galactose.) The CUP1 promoter can be used which is the metallothionein gene promoter. It can be activated by copper or silver ions added to the medium. The PHO5 promoter can be induced in conditions of low or no phosphate in the medium. Steroid inducible expression can be also used to regulate expression of encoded biomolecules.

In one embodiment, one can place the rat glucocorticoid receptor gene behind the constitutive GPD promoter to express the rat glucocorticoid receptor in yeast. A second vector can be made with 3 glucocorticoid response elements upstream of the CYC1 (cytochrome c) gene minimal promoter and the gene of interest to be controlled. This system can work well with dose dependent expression when steroid hormone is added to the medium. Response time is rapid with t1/2 of 7-9 minutes after addition of hormone. Heat shock induced expression can be accomplished by placing the UAS from a heat shock gene in front of a minimal promoter. See, additionally, (1) Schena M. et al., *Science, Aug.* 19, 1988:24 (4868):965-7, (2) Wright et al., *J. Biol. Chem.*, Sep. 5, 1990: 265(25):14763-9.

The cell display can be such that the biomolecules are produced and displayed attached to the cell membrane, cell wall, or cellular appendages such as, for example, flagella, cilia, fimbria, or pilli.

Display can also occur in the cell cytosol, intracellular components, or organelles. In addition, biomolecules can be secreted or released from the host cell.

III. Solid Surface

The solid material having a surface is not particularly limited so long as the expressed biomolecules can be selectively bound to the surface. For example, it can be a crystalline solid material having a surface, or an amorphous solid material having a surface. It can be single crystalline, microcrystalline, nanocrystalline, or polycrystalline. It can be an inorganic or an organic cluster. Or it can be an inorganic solid material having a surface, or it can be an organic solid material having a surface. In addition, it can be a semiconductor material, a metallic material, or a ceramic or glass material having a surface. It can be a polymer material having a surface. Quantum dot solid materials can be used. Composite materials such as fiberglass, wood, and concrete can be used. In general, solid materials having hard surfaces are preferred over solid materials having soft surfaces. Mixtures can be used.

The form of the solid material having a surface is not particularly limited. For example, it can be a non-particulate solid material such as, for example, a films or wafers, or it can be a particulate solid material. The surface can be substantially smooth, planar, or curved. Particulate solid materials can be macroscopically particulate, having lateral dimensions on the orders of millimeters for example. Or they can be microparticulate or nanoparticulate.

Generally, the solid material having a surface can comprise any element in the periodic table. A single crystal, polycrystalline material or nanocrystal, composed of, an element or combination of elements, including but not limited to, Cu, Ag, Au, Fe, $Fe_3O_4$, $Fe_2O_3$, Pt, FePt, Co, CoPt, Sm, $SmCo_5$, Al, AlAs, AlGaAs, Ti, $TiO_2$, Sn, $SnO_2$, Zn, ZnS, ZnSe, ZnTe, Cd, CdS, CdSe, CdTe, Pb, PbS, PbSe, PbTe, Si, Ge, Ga, GaN, AlGaN, InGaN, In, InP, InAs, Ca, $CaCO_3$, $CaPO_4$, and the like. An amorphous material can be used, composed of, but not limited to, the materials described above, and their oxide derivatives. The material can be a metal, an alloy of metals, or metal ions or soluble metal salts, composed of an element or combination of elements including but not limited to, Cu, Ag, Au, Fe, Pt, Co, Sm, Al, Ti, Sn, Zn, Cd, Pb and Ca.

The substrate can be a single crystal, mineral, or wafer. It can be an uncoated nanoparticle or powder.

Metals and magnetic materials can be used including those described in, for example, Belcher et al., patent application Ser. No. 10/665,721, filed Sep. 22, 2003 ("Peptide Mediated Synthesis of Metallic and Magnetic Nanoparticles").

The polymer surface can be, for example, hydrocarbon chain polymers, organic polymers, inorganic polymers, electronic polymers, semiconductor polymers, metallic polymers, polypyrrole, or garment polymers such as, for example, polypropylene or polyester.

The solid material having a surface can be, in addition, a biological polymer such as, for example, spider silk, silkworm silk, collagen, lignin, chitin, cellulose, and derivatives thereof.

Before selective binding, the surface can be treated. Preferably, for example, the solid material having a surface can be treated to limit non-specific interactions between the plurality of expressed biomolecules and the surface. The solid material having a surface can be a monolithic block of material or can be a mixture of materials including, for example, blends, alloys, composites. Solid materials can have a bulk structure which is distinct from a surface structure. Solid materials can be surface oxidized.

Solid materials can be modified to include moieties which have known complementary recognition units for use in selective binding to the biological molecules. For example, nanoparticles can be surface treated to include moieties which extend off of the nanoparticle into the surrounding media, and can recognize and bind to complementary structures.

Although use of solid surfaces is a preferred embodiment, the selective interaction can also be carried out against substrates in solution such as, for example, metal salts and reactive precursors which react to form solid materials in the presence of the biomolecules.

IV. Contacting Step and Conditions for Selective Binding

The contacting step is not particularly limited so long as conditions are provided which allow for selective binding. Methods known in the art can be used to adjust the stringency of the binding including pH adjustment and salt concentration variation. The time of the binding can be adjusted as needed.

Generally aqueous conditions can be used, including aqueous buffer conditions. The temperature is not particularly limited but a temperature of less than about 100° C., and more particularly, less than about 50° C. can be used. A typically good temperature range can be, for example, about 0° C. to about 40° C., and more particularly, about 15° C. to about 40° C. Thermophilic organisms can be used which allow for temperatures to about 100° C.

V. Other Steps and Elements

Once selective binding is carried out, further steps can be carried out comprising the step of isolating expressed biomolecules which selectively bind to the solid material having a surface. Methods known in the art can be used for this isolation including, for example, use of optical, magnetic, electrical, or physical characteristics. In particular, fluorescent and magnetic properties can be used. For example, isolation can be performed on a Flo Cytometer with a magnetic cell separation apparatus. Alternatively, isolation can be carried out with a density gradient, or in a fluidic chamber, or using a centrifugation device.

Clones from the binding populations can be sequenced by methods known in the art including direct sequencing by PCR, or by isolation of DNA from the clone followed by amplification in *E. Coli*. After grouping identical sequences, a plurality of unique sequences can be determined.

Preferably, a high percentage of the clones sequenced from the populations are able to confer binding in a naïve host cell, and preferably this percentage is at least 50%, at least 60%, more preferably, at least 70%, and more preferably, at least 80%, and more preferably at least 90%.

If desired, once selectively bound biomolecules are determined, these biomolecules can be also used for fabrication of materials, particularly the solid material having a surface which was subjected to the selective binding. For example, particulate solid material can be grown in the presence of biomolecules, wherein the selective binding controls factors such as crystal structure, particle size, and temperature of reaction. The solid particulate material can be microparticulate material or nanoparticulate material. Average particle sizes can be, for example, about 2 nm to about 100 nm, about 5 rum to about 50 nm, or about 10 nm to about 25 nm. Additional average particles sized can be, for example, about 100 nm to about one micron, or about one micron to about 500 microns. The particulate materials are not particularly limited but can be, for example, inorganic, organic, magnetic, metallic, electronic, ceramic, oxide, nanocrystalline, quantum dots, semiconductors, and other materials noted above in the description of the solid material having a surface.

Generally, particulate materials can be prepared at relatively low temperatures including, for example, about 300° C. or less, about 100° C. or less, or about 0° C. to about 40° C., or more particularly about 20° C. to about 40° C. Temperatures which are ambient and about room temperature in particular are preferred.

VI. Articles

Articles can be fabricated comprising a solid material having a surface and expressed biomolecules which are selectively bound to the surface and are genetically engineered to selectively bind to the surface. The binding molecules can be prepared directly by genetic engineering, formation of libraries, and biopanning, or can be prepared synthetically based on the results of the biopanning methods. The expressed biomolecules can be expressed in a eukaryotic cell display library.

Films can be formed on the surface including single layer films, multi-layer films, and monolayers. Film thickness is not particularly limited but can be, for example, about 1 nm to about 100 microns, or about 10 nm to about 50 microns, or about 100 nm to about 10 microns.

If desired, high temperatures can be used to eliminate organic materials on the surface and leave residual materials.

VII. Methods of Making, Articles, and Methods of Using

Applications of particular interest including using the methods and compositions described herein to bridge inorganic and organic materials, or bridge inorganic and living materials.

Applications include brew materials with well defined properties and low defect materials; magnetic materials for high-density storage; self-healing coatings; bio-sponge-environmental applications, localization or attachment to specific materials or regions on the materials (e.g., cell-electrode, cell-semiconductor); cell binding to a biological material and a material for transplantation interfaces, image contrast agents, drug delivery, biosensors, cell-based sensors, localizaiton of cells to material surfaces, connecting nerve cells to electrodes, growing quantum dots or other material markers directly on cells, medical implants.

Additional applications of the eukaryotic cell display can be applications of phage virus displays. In particular, applications can be carried out which take the additional properties of yeasts and other eukaryotic cells into account such as, for example:

1) yeast are cheap, produce protein biomolecules at very high yields, and are extremely scalable as evident in, for example, the brewing industry;

2) cells can produce larger, more complex, or post-translationally modified biomolecules at higher copy number;

3) cells are living and growing and thus in applications related to coatings, they can form living coatings or articles which are self-healing;

4) cells have sensory capabilities and can respond to environmental stimuli/conditions. Thus, a biosensor aspect can be combined with any article. For example, a cell can produce a response upon binding to a material, or a cell can respond to a stimulus and then bind a material as in, for example, regulation of display.

Kits can be prepared including combinatorial library kits. For example, kits can be provided for growing materials in solution which include one or more components including (1) a biomolecule to assemble a material from precursors, (2) the precursors which react to form or assemble into the material, (3) accessories such as, for example, tubes, columns, and the like to aid in the process.

Kits can be provided for growing materials on or in cells in, for example, cell labeling. Components can include, for example, (1) DNA encoding a biomolecule to assemble a material from precursors; the DNA can be delivered to a cell which then expresses the biomolecule as a tag (2) the precursors which assemble into the material, and (3) accessories such as, for example, tubes and columns to aid in the process.

Kits can be provided for binding cells to particular materials such as, for example, electrodes. These can include DNA encoding the biomolecule which can mediate binding to the material of interest.

Kits can be provided for detection of particular material surfaces including identification of defects through binding. These can include (1) cells expressing biomolecules, or the biomolecules themselves, which would bind to specific materials; if desired, one can provide an assortment of material-specific clones, (2) instructions on how to bind the cell to materials, and methods of differentiating between materials.

VIII. Further Description of the Invention and Working Examples

The present invention is further illustrated by the working examples and discussion thereof in the following section, which demonstrates that antibodies and peptides can be isolated from a combinatorial library that, when displayed on yeast, mediate interaction with a variety of materials, including II-VI (CdS) and III-V (GaN) semiconductors, a metal (Au), a magnetic alloy (FePt), and an insulator ($Al_2O_3$). As noted above, these classes of materials are becoming increasingly important in developing new types of transistors, amplifiers, photovoltaics, magnetic storage, and light emitting diodes. Methodologies to integrate these and other technologically important materials with biology will aid development of a wide array of applications with potential biotechnological and medical value. An example of where these materials are already impacting biology is the use of II-VI semiconductor quantum dots as optical probes for cellular and subcellular imaging (29). The combinatorial methodology described herein allows one to engineer controllable, specific adhesive interactions between biologicals and electronic, optical, and magnetic materials.

Through this cell panning method scFv fragment polypeptides were identified as well as full-length scFvs, and were material specific as in the case of CdS clone E01. Peptides were sufficient to mediate interaction with a flat material surface, as has been shown using peptides selected by phage display for a variety of materials (3, 4). Although the present invention is not limited by theory, it has been postulated that since peptides have greater conformational freedom than the more structured scFv antibodies, there is a greater probability that a peptide will assume a configuration that results in an energetically favorable interaction with the flat crystalline surface than the probability of a scFv, with perfect or near perfect structure to match a crystalline surface, exists in the library. Furthermore, smaller peptides may express at higher levels than full proteins, and thus contribute through avidity to enhance cell binding. Although represented as only a fraction of the library (less than one-third) (13), fragments with frameshift C-terminal polypeptides were predominantly isolated. Thus, panning a large random peptide library displayed on the cell surface serves to produce material specific peptides as well, complementary to phage panning, yet with ability to directly visualize binding.

Antibodies were also identified after three rounds of panning for the non-metallic crystalline materials CdS, $Al_2O_3$, and GaN. Although frameshifted scFv fragments dominated in these screens as well, this shows that full-length scFvs are capable of interaction with material surfaces. The defined folded structures may mediate more specific or higher affinity interaction with materials if properly folded by reducing the entropic cost of binding. It is expected that refinement of this panning method, for example by using FACS to enrich for fluorescently immunolabeled full-length clones (15) or magnetic bead enrichment (26), will enable better detection of high affinity, material-specific antibodies for various applications. Furthermore, this method may be modified by using suspensions of materials, such as quantum dots (30), or solutes grown into particles (5-7, 31, 32) and screening for clones which interact with or grow such particulate materials by FACS, magnetic (9, 26), or density cell separation procedures. Such screening procedures, such as FACS sorting or magnetic separation, are difficult if not impossible to perform on phage due to the small size and relatively low number of potential bound fluorescent or magnetic units, yet are routinely performed on cells.

The cell panning method was able to identify material specific proteins through relatively simple experimental procedures. Furthermore, direct application of the selected scFv and fragment yeast clones as self-healing biofilms and material discrimination reagents was demonstrated. However, the utility of these selected biomolecules is not limited to display on yeast cells. It is of interest to display such material binding proteins on other eukaryotic cell types to mediate cell-material interaction. For example, current methods used to attach neurons or engineered cells to electrodes can require exogenous adhesion molecules and results in imprecise cell localization (33, 34). The selected proteins provided by the present invention, displayed by human neurons, can enable direct attachment to an Au electrode, or other device, resulting in a direct interface between cell and device. These and similar biomolecular bridges can be used in implants, tissue engineering scaffolds, and medical diagnostics and therapeutics.

Furthermore, cell-based systems are dynamic and have built-in sensory, logic, and response machinery, shown here by the ability of the cells to respond to environmental cues, regulate display, and replicate. Thus, development of sensitive biosensors and biomechanical devices can benefit from effective coupling of cells to specific locations within device architectures.

Finally, engineered cells, especially yeast, can function as biomolecular factories for proteins and peptides (18, 35). One can adapt this synthesis potential of cells to the production of high value materials using material-specific biomolecules to direct the assembly of the materials.

IX. Working Examples

The invention is further illustrated by means of the following non-limiting working examples.

I. Materials and Methods

Yeast Strain and Library.

The human repertoire single chain antibody (scFv) library (13) was maintained as previously described (22). The scFvs fused to the C-terminus of Aga2 are encoded on 2-micron plasmids downstream of a Gal-based promoter, and maintained in yeast strain EBY100 which has Aga1 under control of a Gal-based promoter integrated in its genome (22).

Materials.

Materials were obtained from the following sources: Polished single crystal CdS [A-plate] (Cleveland Crystal), Evaporated Au coated glass slides (Evaporated Metal Films Corporation), FePt thin film on SiN wafer (T. Thomson, IBM, Almaden, Calif.), Epitaxially grown GaN and $Al_2O_3$ template (A. Stonas and E. Hu, UCSB, Calif.). Materials were cleaned after experiments by brief aqueous sonication in a bath sonicator (Fisher Scientific), rinsed in ethanol and stored dry. GaN and $Al_2O_3$ were also subjected to a weak acid wash in 4 mM HCl. Materials were blocked for 1 hr in appropriate panning media prior to use.

Panning Procedure.

In general, selection was carried out by exposing the material to a culture of induced yeast cells in synthetic dropout media supplemented with galactose (SG) (22), washing the material in fresh media, then rescuing the bound cells by trypsinization/triteration in round d1 or growing off in synthetic dropout media supplemented with glucose (SD) (22). Panning rounds d1-d7 were performed under the following conditions at 22° C. Round d1: 150 OD cells in 75 mL SG+5 mg/mL Bovine serum albumin (SG-BSA), 24 hrs incubation; d2: 8 OD cells in 8 mL SG-BSA, 24 hrs incubation; d3: 2 OD cells in 4 mL SG-BSA, 6 hrs incubation; d4: 2 OD cells in 4 mL SG-BSA, 2.25 hrs incubation; d5: 0.2 OD cells in 1.5 mL phosphate buffered saline+5 mg/mL BSA+0.1% tween-20 (PBS-BSAT), 2 hrs incubation; d6: 0.1 OD cells in 1 mL PBS-BSAT, 1 hrs incubation; d7: 0.1 OD cells in 1 mL PBS-BSAT, 45 min incubation. Panning rounds e1-e3 were performed under the following conditions with grow off rescue after each round: Round e1: 250 OD cells in 125 mL SG-BSA, 21.5 hrs incubation; e2: 1.5 OD cells in 3 mL SG-BSA+0.1% tween-20 (SG-BSAT), 2 hrs incubation; e3: 1 OD cells in 1 mL SG-BSAT, 2 hrs incubation.

Cloning of scFv Mutants.

Truncation mutants were constructed using Quickchange mutagenesis (Stratagene) to add stop codons at the desired locations. Oligonucleotide primers for D01I (5'-GGAACTGAGCAGCCTGACTAACGAAGACACGGCCGTC-3' (SEQ ID NO: 3) and 5'-GACGGCCGTGTCTTCGTTAGT-CAGGCTGCTCAGTTCC-3') (SEQ ID NO: 4), D01H(5'-CCTTGAGTGGCAGGGTTAAGATTACCGCGGACACA-3' (SEQ ID NO: 5) and 5'-TGTGTCCGCGGTAATCTTAACCCTGC-CACTCAAGG-3'; SEQ ID NO: 6), D07V(5'-CACCATGACCAGGGACTAACATCACCACGGCCGAC-3' (SEQ ID NO: 7) and 5'-GTCGGCCGTGGTGATGTTAGTC-CCTGGTCATGGTG-3') (SEQ ID NO: 8), D07R(5'-GGCT-TGAGTGGATGGGATAGATCAACCCTAGCAGTGG-3' (SEQ ID NO: 9) and 5'-CCACTGCTAGGGTTGATCTATC-CCATCCACTCAAGCC-3') (SEQ ID NO: 10), E01V(5'-CACCATGACCAGGGACTAACATCACCACGGCCGAC-3' (SEQ ID NO: 11) and 5'-GTCGGCCGTGGTGATGTTAGTCCCTGGT-CATGGTG-3'; SEQ ID NO: 12), and E01R (5'-GGCT-TGAGTGGATGGGATAGATCAACCCTAACAGTGGTG-3' (SEQ ID NO: 13) and 5'-CACCACTGTTAGGGTTGATCTATC-CCATCCACTCAAGCC-3'; SEQ ID NO: 14) were used with plasmid DNA isolated from clones D01, D07, and E01 as template. Mutants corresponding to distal peptide fragments lacking the $V_H$ regions were cloned by generating dsDNA inserts from oligonucleotides for D01pep (5'-CCCGGGGCTAGCGGTGGCGGCCATGAT-TACAGAGGTCATATTCATGGTCATTCTC AACATGG-TACTGAACAACCAGATTAGGATCCGATCAG-3'; SEQ ID NO: 15), D07pep (5'-CCCGGGGCTAGCGGTGGCG-GCGATGTTCATCATCATGGTAGACATGGTGCTGAA CATGCTGATATTTAGGATCCGATCAG-3'; SEQ ID NO: 16), and E01pep (5'-CCCGGGGCTAGCGGTGGCGGC-GATGTTCATCATCATGGTAGACATGGTGCTGAA CAAGCTGAAATTTAGGATCCGATCAG-3'; SEQ ID NO: 17) annealed to a primer (5'-ATCCCGGGGCTAGCGGTG-GCGGC-3'; SEQ ID NO: 18) and extended using Expand Enzyme (Roche Diagnostics). Inserts were digested NheI/BamHI and cloned into NheI/BamHI digested pCTCON, resulting in fusion of the peptides at the end of a $(G_4S)_3$ flexible linker in the same context as the scFvs. Sequenced plasmid DNAs harboring these cloned mutants and peptides were transformed into EBY100 using the Geitz transformation kit (Tetralink).

Clonal Verification and Material Specificity Binding Assays.

Cells transformed with plasmid DNA were grown to mid-log phase in SD at 30° C. then induced in SG for 18 to 24 hrs at RT. 2 $OD_{600}$ units of cells were resuspended in 1.5 mL SG-BSAT in 2 mL microcentrifuge tubes. Pre-blocked 0.5 cm² CdS was added to each clone culture and rocked for 1 h, washed in SG-BSAT in new tubes for 30 min., and transferred to 6-well culture plate for light microscopy imaging. For clone E01 specificity assay, all materials were placed in a culture flask containing 20 $OD_{600}$ units of cells in 20 mLs SG-BSAT for 1 h, washed for 1 h, and imaged as above.

Optical Microscopy and Cell Quantitation.

Digital images were collected with a AxioCam MR on a Axioplan optical microscope (Carl Zeiss Inc.), and percent area coverage was quantified by using ImageJ v1.3 developed by Wayne Rasband, NIH. Briefly, images were converted to binary by adjusting the threshold to differentiate between cell and background areas. The particle analyzer function (particle size range 10-10⁵ pixels) was used to calculate the fraction of total area covered by cells. Values for each clone were derived from 675 µm×535 µm total area and averaged from 3 images taken from each of 2-4 independent experiments.

Biofilms.

On Au: A 4 cm² Au coated slide was incubated in SG-BSAT with 0.1 $OD_{600}$/mL uninduced clone A02 (Table II) in a 6-well plate and rocked for 12 h at RT. The Au slide was then transferred to fresh SG-BSAT and placed on the rocker. 32X images were taken at various time points during biofilm growth: Pre-binding (t=0) and at 12 (time of transfer), 24, 36, and 48 h. On CdS: A 0.5 cm² polished CdS single crystal was incubated with 1 $OD_{600}$/mL pre-induced clone D07 for 1 h at RT on a rocker. The CdS was then placed into a 6-well plate with fresh SG-BSAT. A pattern of cells was cleared from the surface of CdS using a pipette tip and 5× images taken at this point (t=0 h) and after 24 and 48 h growth.

Biomolecule Templated Quantum Dots.

A CdS clone, as a soluble peptide, was tested for the ability to direct fluorescent, photoluminescent nanoparticle assembly. The synthetic peptides tested were the CdS binding D07pep clone (biot-SGGGDVHHHGRHGAEHADI-c, NewEngland Peptide, Inc.) (SEQ ID NO: 1) and FP-1 peptide (n-HNKHLPSTQPLA-c (SEQ ID NO: 2), MIT biopolymers laboratory) as a negative control.

Figure 7:
FIG. 7. Fluorescence from biomolecule templated CdS nanoparticles. Upon exposure to a UV light source, intense fluorescence was observed from samples with the synthesized D07peptide (biot-SGGGDVHHHGRHGAEHADI-c,) (SEQ ID NO: 1) mixed with the metal salts (center), but not from peptide D07 alone or the metal salts alone (left). The control peptide FP-1 (n-HNKHLPSTQPLA-c) (SEQ ID NO: 2) mixed with metal salts (right) resulted in marginal fluorescence when mixed 1:1 and no fluorescence when mixed 1:10 with the metal salts. Concentrations of peptides and metal salts are shown in the figure. All reactions were performed at room temperature, standard atmospheric pressure in water.
Figure 8:
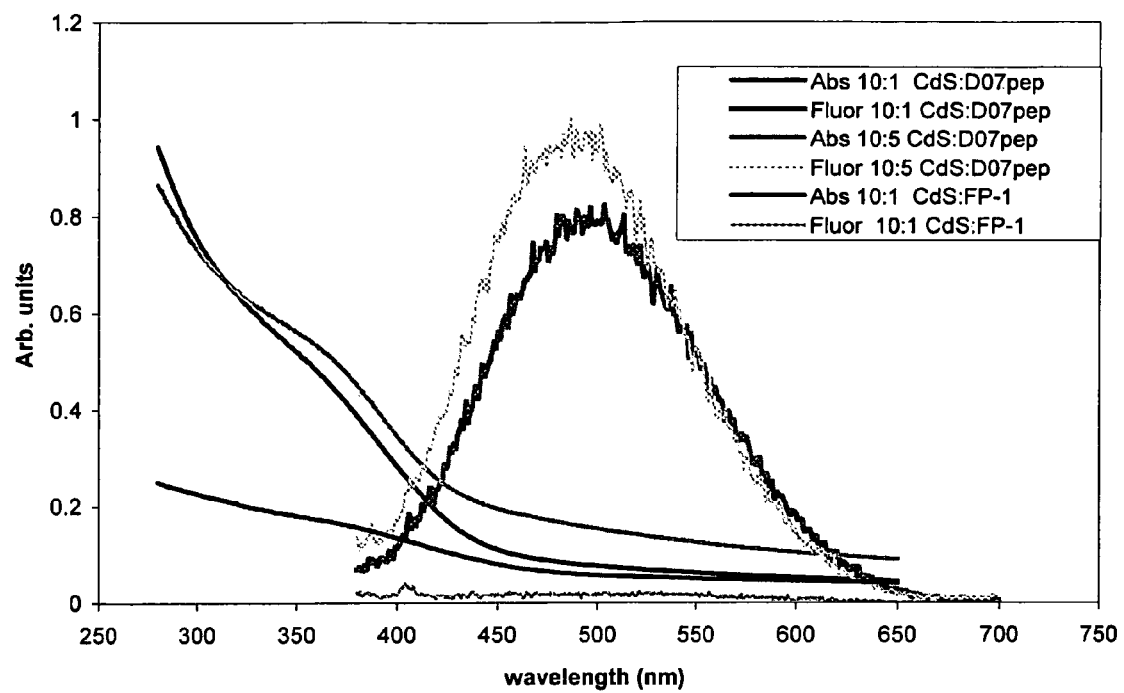
FIG. 8. Absorbance and photoluminescence spectra of CdS nanoparticles grown in the presence of D07peptide or control peptide FP-1. D07 peptide grown particles show absorption fronts between 400-450 nm and corresponding fluorescence peaks (maximum ~500 nm), characteristic of nanoparticles exhibiting quantum confinement effects. Alternatively, particles grown with control peptide FP-1 show a weak absorbance front closer to the 515 nm of bulk CdS and display only weak, if any, fluorescence. Concentrations designated as ratios range from 325 uM (ratio=10) to 32 uM (ratio=1).

CdS quantum dots were formed at room temperature in aqueous conditions simply by mixing a selected peptide derived from clone D07pep with metal salts. In brief, the synthesized CdS D07 peptide and a negative control FePt binding sequence FP-1 were dissolved in water at room temperature and mixed with aqueous $CdCl_2$. Aqueous $Na_2S$ was then slowly added to these vigorously stirring solutions until equimolar concentrations of Cd and S were reached (325 µM each). Particles grown in various molar compositions of peptides were exposed to long wavelength UV light for quick fluorescence visualization (FIG. 7). With tuning of growth conditions, control over size and fluorescent properties of such biomolecule templated nanoparticles can be controlled. Absorbance spectra were taken on as prepared particles using a DU800 spectrophotometer from Beckman Coulter (FIG. 8). Photoluminescence emission spectra were taken on a PTI fluorometer with excitation at 360 nm (FIG. 8).

II. Results

Panning.

A non-immune library of 10⁹ human scFv antibodies displayed on *S. cerevisiae* (13) was first panned against single crystal cadmium sulfide (CdS), a II-VI semiconductor. Sequential rounds of screening (d1-d7), were performed on a 1.0 cm² polished CdS single crystal [A-plate] to identify material specific clones. The surface of the CdS was first blocked in SG (23) containing 5 mg/mL BSA to limit non-specific interactions before each round. The CdS was then exposed to the yeast library in an aqueous buffered environment for 1-24 h, washed in media, and visualized by light microscopy (FIG. 1A). The bound yeast were then permitted to "grow off" the surface by placing the CdS in glucose-based SD (23), which turns off expression of the scFvs fused to Aga2, and cultured for 24 h (FIG. 1A inset). The "grow off" method ensures rescue of all clones bound to the material. Rounds d1-d4 were screened in SG-BSA while rounds d5-d7 were screened for shorter time periods in PBS-BSAT, which contains tween-20, to increase the stringency of selection.

In comparison, a control yeast clone expressing a fragment of the CD20 ectodomain, CTCON (13), was contacted with CdS under identical conditions as the library in FIG. 1A, yet was unable to bind (FIG. 1B). Even after attempting to grow off any bound cells by 24 h in SD, the cultures remained clear (FIG. 1B inset). Other controls were performed on round 3 sub-libraries. Screening buffer without BSA resulted in increased cell coverage of the material surface versus buffer with BSA (data not shown), indicating BSA-independent binding of the clones to the CdS surface and the usefulness of a non-specific blocking agent. Also, binding to the materials was observed in both SD and SG when an induced culture was used, showing that the sugar molecules themselves did not affect binding. Further, binding was also observed in PBS-based buffers that lacked yeast nutritional components (data not shown). Together these experiments demonstrated that binding was medium independent, but dependent upon the displayed library.

Figure 5:
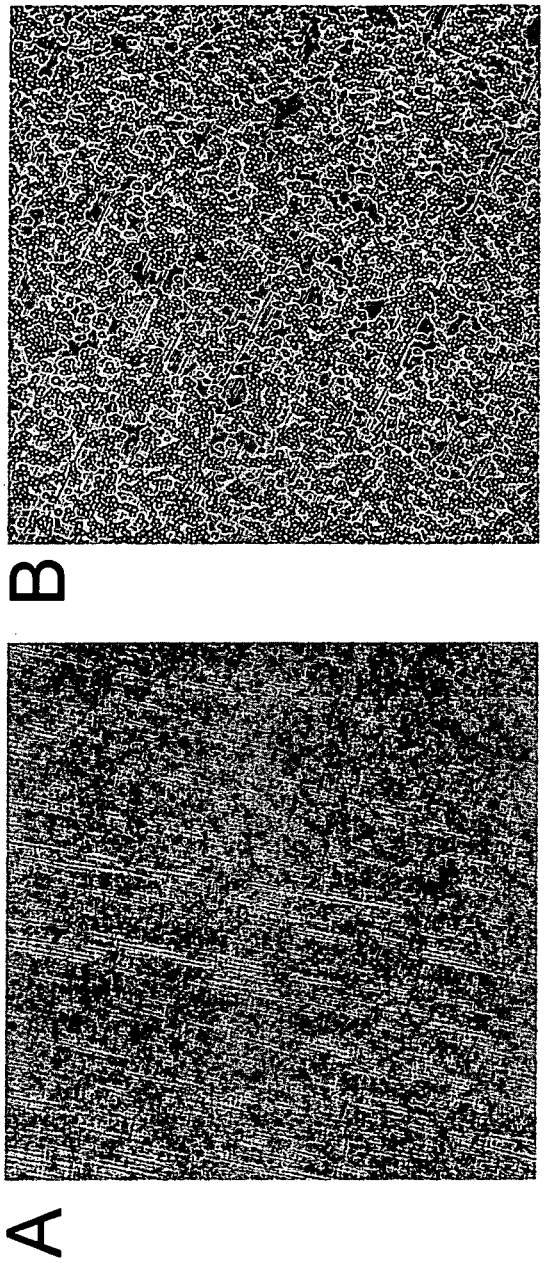
FIG. 5. Genetic regulation of binding. The d7 population of yeast clones selected by panning against CdS single crystal were grown in glucose medium. (A) Without antibody library expression, cells do not bind the CdS single crystal. (B) The same cells switched into galactose medium (SG) bound CdS, showing the interaction was dependent on library expression. Transmission light microscopy image were ca. 540 µm×540 µm in size.

The ability to regulate the binding of the cells to the material through control of gene expression was then explored. Importantly, media with glucose (SD) repressed expression of the scFvs, while a switch to galactose (SG) induced expression roughly 1000 fold over the repressed state as shown previously (23). Clones grown in SD exhibited no binding in comparison to identical cultures grown in SG (FIG. 5). Thus, interactions with the surface of CdS were mediated through the displayed antibody fragments, and were nutritionally regulatable.

After round d7, a total of 36 yeast clones from the selected binding population were sequenced. DNA was isolated from each yeast clone, amplified in *Escherichia coli*, isolated and sequenced by common methods. Three unique CdS clones, D01, D07, and E01, were identified after grouping identical DNA sequences, and were represented 26, 6, and 4 times, respectively. The sequences were translated and aligned with consensus IgG Fv domain sequences using IgG BLAST (available on the NIH website), and residues differing from the consensus were identified (Table I). The DNAs corresponding to these groups were then transformed back into naïve EBY100 yeast and clones were tested again for binding to CdS, to eliminate false positives due to host chromosomal mutations. All three CdS-binding sequences reconfirmed their original phenotype in the clonal verification binding assay (Materials and Methods). The results are quantitatively displayed in FIG. 2A as percent area coverage of the CdS surface.

Using image analysis software, D01 covered 48%, D07 covered 50%, and E01 covered 40% of the surface of the CdS. The theoretical maximum for surface area coverage from the footprint of hexagonally packed perfect spheres was about 90.7%. However, the yeast are not uniform in size, they can have buds, and lateral forces to move the cells were insufficient to maximize the packing of the randomly adhered yeast cells. Therefore, based on an average separation distance between hexagonally packed perfect spheres of one-half their diameter, the theoretical maximum footprint coverage reduced to about 41%. Thus, the coverage observed for D07 likely represents a maximum surface coverage by a single monolayer of randomly adhered cells.

As seen in Table I, all three CdS clones were fragments of full-length scFvs, which upon analysis of DNA sequence appeared to have originated from frameshift mutations present in the natural antibody repertoire or introduced during PCR construction of the library. Feldhaus et al reported 68% of the library to express the distal c-myc epitope (13), thus a maximum of about one-third of the library may express scFv truncations. The resulting D01, D07, and E01 polypeptides are comprised of 47, 70, and 70 amino acids with 100, 91, and 90% homology to class $V_H 6$-1, $V_H 1$-2, and $V_H 1$-2 variable heavy chain domains, followed by 33, 13, and 13 amino acids, respectively, with no resemblance to the natural contiguous $V_H$ sequences. The composition of the "frameshift" amino acids was predominantly polar and charged residues, significantly enriched in histidine.

Truncation mutants derived from each CdS clone were created (Table I) and tested for binding to CdS (FIG. 2A) in order to determine regions necessary for binding. D01I, which removed only half of the C-terminal "frameshift" amino acids from D01, bound to CdS. Removal of the entire frameshift region (clone D01H) abolished binding, which suggested that the frameshift region is necessary for mediating the yeast-material interaction. Similarly, D07V and E01V, which removed all C-terminal frameshift amino acids from clones D07 and E01, respectively, did not show any ability to mediate CdS binding. As expected, further truncations that removed the CDR2 and C-terminal peptide region (D07R and E01R) did not show any binding. Thus we hypothesized that the short peptides attached at the C-terminus of the antibody framework fragments contributed much of the binding energy that held the yeast cells to the surface of CdS.

To test whether the peptides alone were sufficient to bind the yeast cells to the surface of CdS, we constructed Aga2 fusions of the peptides. Here the peptides were displayed without the antibody framework (Table I), attached directly to the long flexible -$(G_4S)_3$AS-linker (SEQ ID NO: 19) at the C-terminus of Aga2 as were the scFvs (13) with an additional-GGG-spacer. These peptides were panned in parallel with the truncations and the original selected clones to determine relative binding efficiencies (FIG. 2A). Clones expressing D07pep were able to bind to CdS, clearly demonstrating the importance of the frameshift region in the original isolated D07 clone. E01pep and D01pep also showed detectable binding, albeit at seemingly lower adhesion strength. The decreased surface coverage of yeast expressing the peptides compared to the parent sequences suggested that the antibody framework provided improved display levels or more accessible orientation for the peptides. These results also demonstrated that E01pep was a weaker binder than D07pep, which was surprising since the peptides differed by only 2 of 15 amino acid residues (HHHGRHGAE[Q/H]A[D/E]I) (SEQ ID NO: 20).

Based on a rigid smooth spherical cell with 2 μm radius sitting on a flat material surface, we estimate that about 2.25% of the surface area of a single cell lies within 5 nm of that material. Assuming approximately $10^4$-$10^5$ evenly distributed peptides per cell (15, 24), and a necessary <5 nm distance for interaction between a displayed peptide and the material, there are on order of 200-2000 potentially surface-interacting polypeptides. Thus differences in relative binding strength may be amplified or masked by avidity effects resulting from multiple peptide-material interactions.

Material Specificity of CdS Clone.

Other technologically important materials were chosen to test specificity of the selected clones for the CdS single crystal. Single crystal sapphire ($Al_2O_3$), epitaxially grown gallium nitride (GaN), polycrystalline gold (Au) sputter coated onto glass, iron platinum (FePt) thin film on Si/SiN, and the CdS were exposed to the CdS clones under identical conditions (Materials and Methods). Clone E01 exhibited exceptional specificity for CdS over $Al_2O_3$, GaN, and Au, as seen by the lack of cells on these materials (FIG. 2B). Clone E01 also showed marked preference for CdS over FePt, even though some binding does occur. However, this FePt thin film has been observed to bind other clones in an apparently less-specific manner. Thus, this system is amenable to identifying material specific protein biomolecules.

Broadly Applicable Method.

Figure 3:
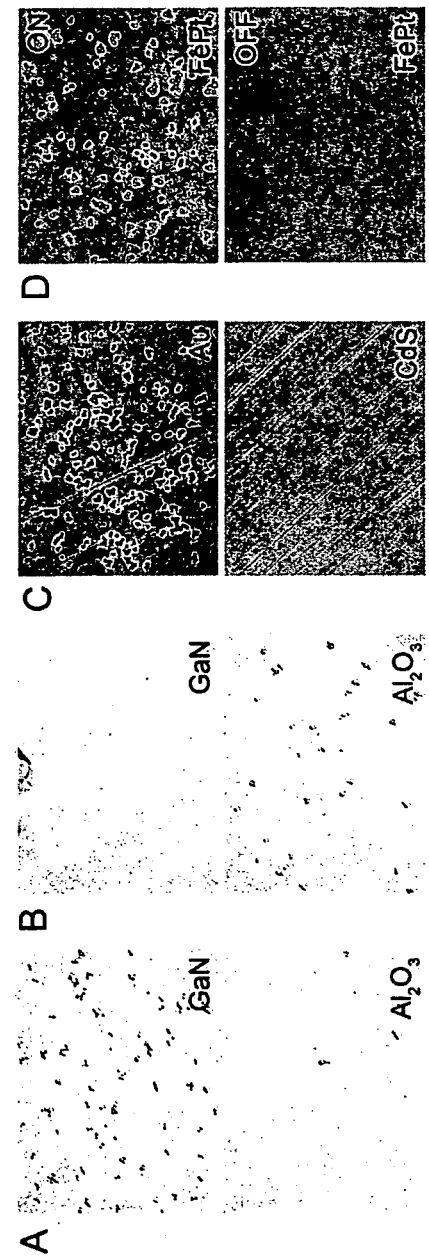
FIG. 3. Examples of binding clones isolated by panning against diverse materials. Sequences identified from panning round e3 were expressed in yeast. (A) 4H01, a full-length scFv antibody, selectively bound to $Al_2O_3$ over GaN. (B) 4H09, a full-length scFv antibody, selectively bound to GaN over $Al_2O_3$. (C) A02, a scFv fragment (Table II), selectively bound to Au over CdS. (D) G02, a scFv fragment (Table II), bound FePt when displayed (ON), but not when expression was repressed by glucose (OFF). Light microscopy images were ca. 340 µm×260 µm.

Other materials were also used in panning experiments in order to demonstrate the universal utility of this method. Three rounds of panning were performed (e1-e3) on $Al_2O_3$, GaN, Au, FePt, and CdS before individual clones were sequenced (Materials and Methods). In addition, the same controls using CTCON and the other aqueous media were performed, as described for CdS to show that binding was dependent upon display, which yielded similar results. FIG. 3 shows selected clones binding to $Al_2O_3$, GaN, Au and FePt. These yeast clones were created from naïve cells transformed with DNA isolated from clones identified by panning against $Al_2O_3$, GaN, Au, and FePt, to their respective materials, and thus are specific binders. Also shown is material specificity of clone 4H01 for $Al_2O_3$ over GaN (FIG. 3A), clone 4H09 for GaN over $Al_2O_3$ (FIG. 3B), and clone A02 for Au over CdS (FIG. 3C), and nutritional regulation of binding of Clone G02 to FePt (FIG. 3D).

Interestingly, only 14 full-length scFv sequences were identified from over 350 DNA sequences from round e3, which grouped into 2 full-length clones for $Al_2O_3$, 3 clones for GaN, 1 clone for CdS, and zero clones for both Au and FePt. The remaining groups with representations ranging from 2 to 26 sequences were predominantly scFv fragments as seen for the original CdS screen. The enrichment of truncated scFvs in 3 rounds of selection to over 96% from an initial representation in the non-selected library of about 30% suggests a bias against full-length clones in our panning for material surfaces. Identification of full-length scFvs from this library in the future could be enhanced by combining the panning procedure with alternating rounds of FACS, a powerful tool used extensively to screen this and other cell based libraries (13, 25), or magnetic bead enrichment (26), for the presence of the C-terminal c-myc epitope tag.

Additionally, Au and FePt were panned in an identical manner as CdS rounds d1-d7 to show reproducibility. From 36 and 23 sequenced clones, there were no full-length antibodies identified for Au or FePt, respectively. A total of 3 Au clones (sequence representation 13, 5, and 2) and 4 FePt clones (sequence representation 16, 1, 1, and 1) conferred binding after isolation and retransformation of the expression plasmid. Thus, 100, 56, and 87% of the sequences from the CdS, Au, and FePt d7 populations were able to confer binding in a naïve host cell. The ability of the false positive clones to survive through 7 rounds of screening was likely due to the fact that Au and FePt were deposited onto other materials. Au was coated onto glass, and therefore presented $SiO_2$ edge surfaces, and FePt was coated onto a SiN wafer, and therefore presented SiN and likely $SiO_2$ as well. CdS on the other hand, was used in the panning as an unattached single crystal, which eliminated potential contamination of the true binders by clones binding to surfaces other than the material of interest. We also compared binding of the Au clones to single crystal Au and the polycrystalline Au, and both were bound with equal numbers of cells per unit area.

Figure 6:
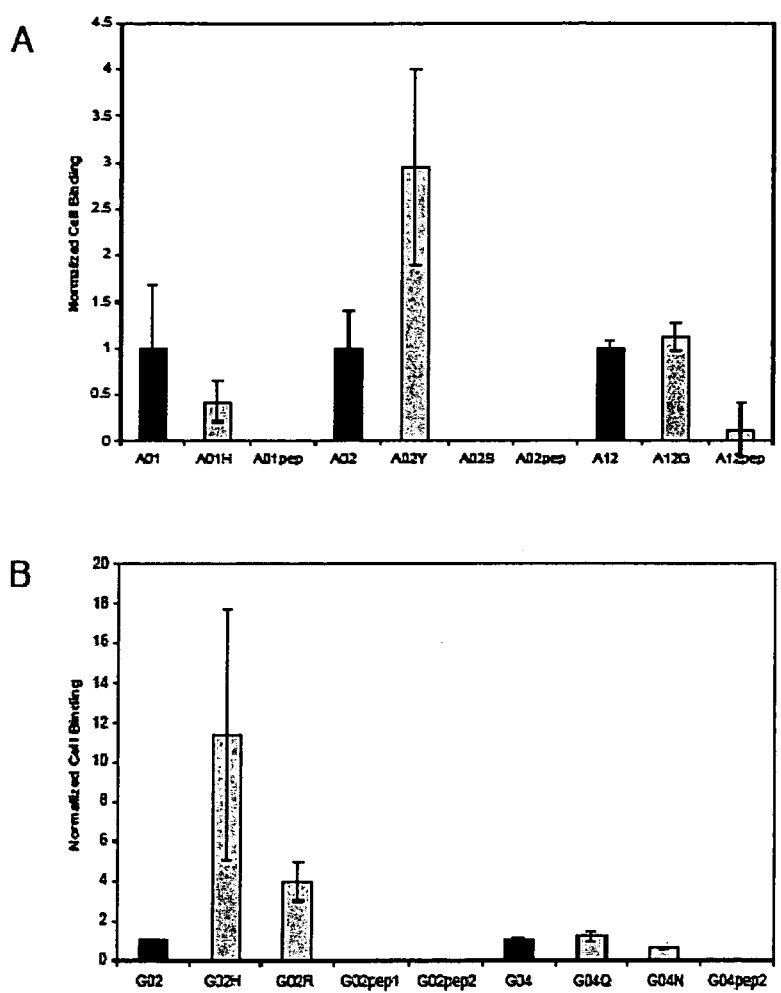
FIG. 6. Relative binding of isolated clones vs. mutants to Au or FePt. Images of isolated clones and designed mutants (see Table II) bound to Au (A) or FePt (B) were used to calculate the number of cells bound on the Au surface. Cell binding numbers for mutant clones (light grey bars) were normalized relative to their respective parent clones (dark grey bars). Values listed are geometric averages from images taken from multiple experiments±std deviation.

Three Au clones, A01, A02, and A12 and two FePt clones, G02 and G04, confirmed by phenotype transfer as true binders to Au and FePt, respectively, were analyzed further. All of these sequences contained a mutation in their $V_H$ domain that lead to frame-shifted peptide sequence terminated by a stop codon (Table II). Similar mutational analysis procedures as shown for the CdS-specific polypeptides in Table 1 and FIG. 2A were performed on these Au and FePt clones. Truncation of the Au and FePt clones removing only the frameshift regions did not completely abolish binding (FIG. 6). Furthermore, in contrast to the CdS clones, C-terminal peptides derived from the frameshift sequences were insufficient to bind yeast to the materials. Thus, the scFv antibody framework appeared important for either direct contribution to binding or for presenting the C-terminal peptides in a favorable conformation.

Application of Material Specific Display.

Figure 4:
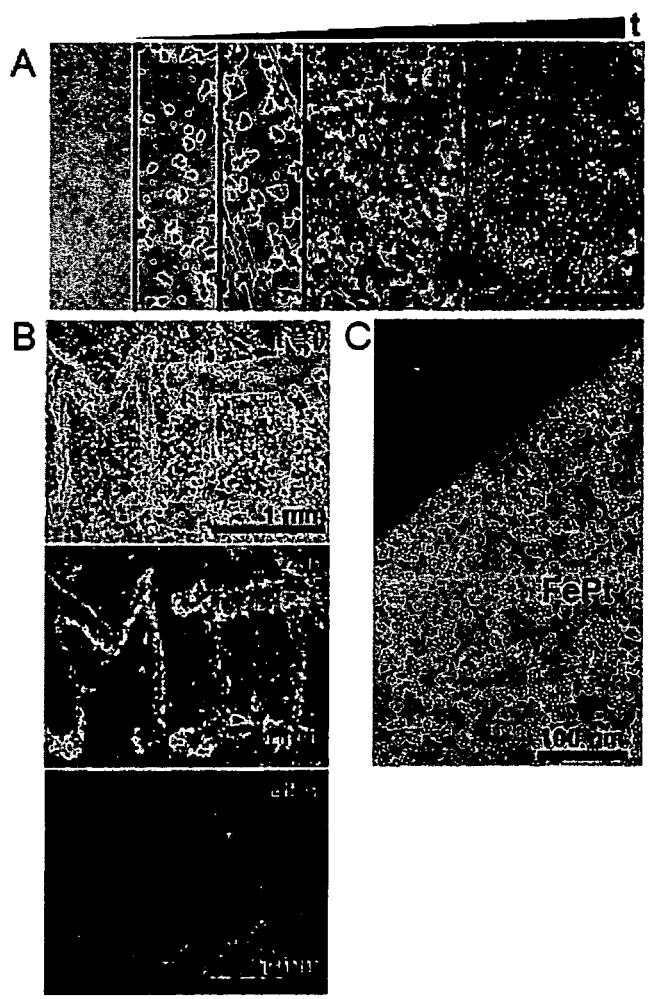
FIG. 4. Applications of yeast expressing novel material interacting proteins. (A) Biofilm coating Au surface was created by growing yeast clone A02 over a 2 d period. (B) A selected portion of bound cells expressing CdS clone D01 were cleared from the surface of CdS at t=0. After 24 h growth, cells were observed to bind to the cleared areas. By 48 h, the biofilm completely self-healed. (C) Labeling of a metal-insulator heterostructure with material specific yeast. Clone G02 binds selectively to FePt over SiN and $SiO_2$. Scale bars shown on each image.

Yeast displaying scFvs and fragments were used to demonstrate potential application of cell-material specific interactions (FIG. 4). Clone A02, a gold binding fragment, was grown in SD and contacted with an Au-coated slide (Materials and Methods). At t=0, no cells bound, as expected. However, over the course of 48 h at RT, cells bound to Au, and continued to grow, bind, and spread, eventually completely covering the slide (FIG. 4A). This living coating, or biofilm, was able to adhere and grow into regions cleared by disturbance, thus was self-healing. CdS clone D07 was used to illustrate the ability of such biofilm coatings to grow and self-heal (FIG. 4B). Even after over three weeks in SG, the biofilm remained attached to CdS and able to regenerate. Such self-healing biofilms can be useful for corrosion prevention, bioremediation, medical (27), or other applications (28).

Use was demonstrated of the selected clones to aid in detection and identification of regions of a surface with particular compositions. For example, clone G02, a FePt binder, was used to detect FePt over $SiN/SiO_2$, as seen by cells covering the region of the heterostructure containing of Fe and Pt, and not on the Si containing region (FIG. 4C). Similarly, as shown in FIG. 2B, the CdS clone bound only to CdS when CdS, Au, GaN, and $Al_2O_3$ were placed in the same culture flask. Thus, these selected protein biomolecules can function as material specific probes, as well as adhere cells to specific locations on a hetero-surface.

Templating.

The selected biomolecules were also used to template the growth of semiconductor nanoparticles. CdS quantum dots were formed at room temperature in aqueous conditions simply by mixing a synthetic peptide derived from clone D07pep with solutions of metal salts. Particles grown in various molar compositions of peptides were exposed to long wavelength UV light for quick visualization of fluorescence (FIG. 7). The D07peptide grown particles show absorption fronts between 400-450 nm and corresponding fluorescence peaks (maximum about 500 nm) characteristic of nanoparticles exhibiting quantum confinement effects (FIG. 8). Alternatively, particles grown with control peptide FP-1 show a weak absorbance front closer to the 515 nm of bulk CdS and display only weak, if any, fluorescence (FIG. 8). With tuning of growth conditions, better control over size and fluorescent properties of such biomolecule templated nanoparticles can be achieved.

Competitive Binding.

Figure 2:
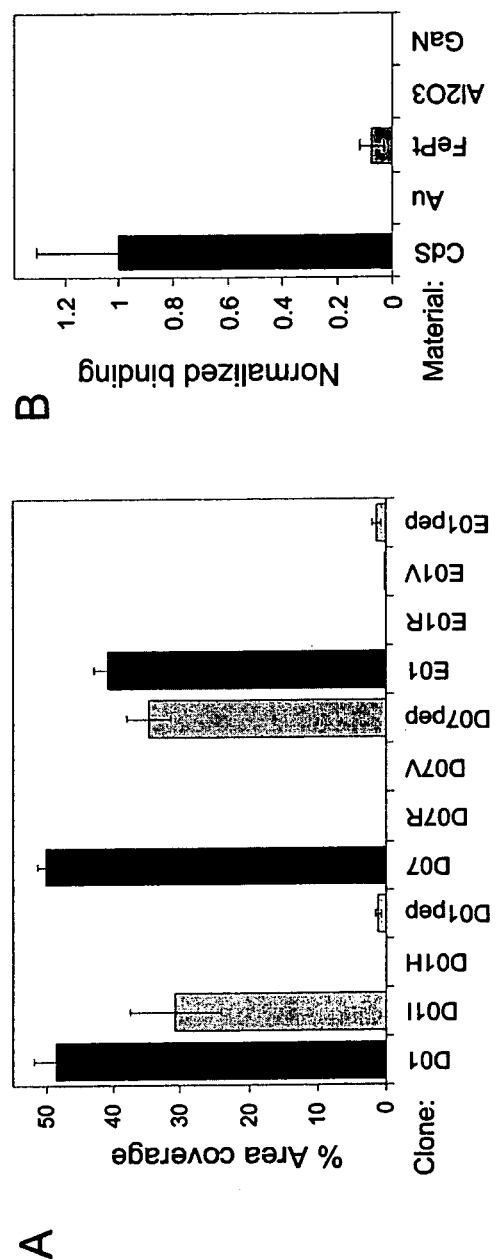
FIG. 2. Quantification of Cell Binding to CdS. (A) Percent surface area covered by cells was calculated from images of isolated clones and designed mutants (Table I) bound to CdS. Parent clones shown as dark grey bars, mutants as light grey bars. (B) Results from CdS clone E01 tested for binding to a diverse collection of materials: Single crystal CdS, Au evaporated onto glass, thin film FePt, single crystal $Al_2O_3$, and epitaxially grown GaN, were normalized to CdS. Values listed are geometric averages from images taken from multiple experiments±std. deviation.

FIG. 2 shows the CdS peptide sequences fused to Aga2 to be necessary and sufficient for mediating CdS-specific yeast binding. Additionally, similar CdS binding studies were performed with these yeast clones in the presence of free D07 peptide. In brief, yeast clones displaying D07 or D07pep as Aga2 fusions (Table 1) were incubated in media (1.5 OD/ml)

with single crystal CdS±37 µM free D07 peptide, washed in media, and imaged by light microscopy. In both cases, free peptide blocked binding of the yeast to CdS, providing further information on the mechanism of binding.

REFERENCES

Finally, the invention can be practiced with reference to the following technical literature:

REFERENCES

1. Georgiou, G., Stathopoulos, C., Daugherty, P. S., Nayak, A. R., Iverson, B. L. & Curtiss, R., 3rd (1997) *Nat Biotechnol* 15, 29-34.
2. Wittrup, K. D. (2001) *Curr Opin Biotechnol* 12, 395-9.
3. Flynn, C. E., Lee, S.-W., Peelle, B. R. & Belcher, A. M. (2003) *Acta Mater.*, Vol. 13, 2413-2421 (2003).
4. Whaley, S. R., English, D. S., Hu, E. L., Barbara, P. F. & Belcher, A. M. (2000) *Nature* 405, 665-668.
5. Lee, S. W., Mao, C., Flynn, C. E. & Belcher, A. M. (2002) *Science* 296, 892-5.
6. Naik, R. R., Stringer, S. J., Agarwal, G., Jones, S. E. & Stone, M. O. (2002) *Nat Mater* 1, 169-72.
7. Mao, C., Flynn, C. E., Hayhurst, A., Sweeney, R., Qi, J., Georgiou, G., Iverson, B. & Belcher, A. M. (2003) *Proc Natl Acad Sci USA.* 100, 6946-51.
8. Wang, S., Humphreys, E. S., Chung, S. Y., Delduco, D. F., Lustig, S. R., Wang, H., Parker, K. N., Rizzo, N. W., Subramoney, S., Chiang, Y. M. & Jagota, A. (2003) *Nat Mater* 2, 196-200.
9. Brown, S. (1992) *Proc. Natl. Acad. Sci.* 89, 8651.
10. Brown, S. (1997) *Nature Biotechnol.* 15, 269-72.
11. Brown, S., Sarikaya, M. & Johnson, E. (2000) *J Mol Biol* 299, 725-35.
12. Braden, B. C., Goldbaum, F. A., Chen, B. X., Kirschner, A. N., Wilson, S. R. & Erlanger, B. F. (2000) *Proc Natl Acad Sci USA* 97, 12193-7.
13. Feldhaus, M. J., Siegel, R. W., Opresko, L. K., Coleman, J. R., Feldhaus, J. M., Yeung, Y. A., Cochran, J. R., Heinzelman, P., Colby, D., Swers, J., Graff, C., Wiley, H. S. & Wittrup, K. D. (2003) *Nat Biotechnol* 21, 163-70.
14. Kieke, M. C., Shusta, E. V., Boder, E. T., Teyton, L., Wittrup, K. D. & Kranz, D. M. (1999) *Proc Natl Acad Sci USA* 96, 5651-6.
15. Boder, E. T. & Wittrup, K. D. (1997) *Nat Biotechnol* 15, 553-7.
16. Peelle, B., Lorens, J., Li, W., Bogenberger, J., Payan, D. G. & Anderson, D. C. (2001) *Chem Biol* 8, 521-34.
17. Bhatia, S. K., Swers, J. S., Camphausen, R. T., Wittrup, K. D. & Hammer, D. A. (2003) *Biotechnol Prog* 19, 1033-7.
18. Cereghino, G. P. & Cregg, J. M. (1999) *Curr Opin Biotechnol* 10, 422-7.
19. Mann, S. (2000) *Angew Chem Int Ed Engl* 39, 3392-3406.
20. Mann, S. (2001) *Biomineralization: principles and concepts in bioinorganic materials chemistry* (Oxford University Press, Oxford; N.Y.).
21. Baeuerlein, E. (2000) *Biomineralization: from biology to biotechnology and medical application* (Wiley-VCH, Weinheim; N.Y.).
22. Boder, E. T. & Wittrup, K. D. (2000) *Methods Enzymol* 328, 430-44.
23. Boder, E. T. & Wittrup, K. D. (1998) *Biotechnol Prog* 14, 55-62.
24. Boder, E. T., Midelfort, K. S. & Wittrup, K. D. (2000) *Proc Natl Acad Sci USA* 97, 10701-5.
25. Daugherty, P. S., Iverson, B. L. & Georgiou, G. (2000) *J Immunol Methods* 243, 211-27.
26. Yeung, Y. A. & Wittrup, K. D. (2002) *Biotechnol Prog* 18, 212-20.
27. Kuhn, D. M., Chandra, J., Mukherjee, P. K. & Ghannoum, M. A. (2002) *Infect Immun* 70, 878-88.
28. Reynolds, T. B. & Fink, G. R. (2001) *Science* 291, 878-81.
29. Wu, X., Liu, H., Liu, J., Haley, K. N., Treadway, J. A., Larson, J. P., Ge, N., Peale, F. & Bruchez, M. P. (2003) *Nat Biotechnol* 21, 41-6.
30. Bruchez, M., Jr., Moronne, M., Gin, P., Weiss, S. & Alivisatos, A. P. (1998) *Science* 281, 2013-2016.
31. Mann, S., Shenton, W., Li, M., Connolly, S. & Fitzmaurice, D. (2000) *Adv. Mater.* 12, 147-150.
32. Flynn, C. E., Mao, C., Hayhurst, A., Williams, J. L., Georgiou, G., Iverson, B. & Belcher, A. M. (2003) *J. Mater. Chem.* 13, 2414-2421.
33. Straub, B., Meyer, E. & Fromherz, P. (2001) *Nat Biotechnol* 19, 121-4.
34. Chiappalone, M., Vato, A., Tedesco, M. B., Marcoli, M., Davide, F. & Martinoia, S. (2003) *Biosens Bioelectron* 18, 627-34.
35. Romanos, M. A., Scorer, C. A. & Clare, J. J. (1992) *Yeast* 8, 423-88.

Additional references are also cited in U.S. Pat. No. 6,331,391 at col. 39-41 which can be used by one skilled in the art to practice the invention.

Although the foregoing invention has been described in some detail by way of illustration and example for purposes of clarity of understanding, it will be readily apparent to one skilled in the art in light of the teachings of the invention that certain changes and modifications may be made thereto without departing from the spirit or scope of the appended claims.

TABLE I

Isolated CdS binding sequences and designed mutants (SEQ ID NOS 22-33, respectively, in order of appearance; SEQ ID NOS 19 and 21 are disclosed below the table).

| Clone | FWR1[a,b] | CDR1[b] | FWR2 | CDR2[b] | FWR3[b] |
|---|---|---|---|---|---|
| D01 | -QVQLQQSGPGLVKPSQTLSLTCAISGDSVS | SNSAAWN | WIRQSPSRGLEWQG | HDYRGHIHGHSQHGTEQP | DIRRHGRLLLCERCN\* |
| D01I | -QVQLQQSGPGLVKPSQTLSLTCAISGDSVS | SNSAAWN | WIRQSPSRGLEWQG | HDYRGHIHGHSQHGTEQP | D\* |
| D01H | -QVQLQQSGPGLVKPSQTLSLTCAISGDSVS | SNSAAWN | WIRQSPSRGLEWQG | \* | |
| D01pep[c] | | | | -HDYRGHIHGHSQHGTEQP | D\* |
| D07 | -QVQLVQSGAEVKKPGASVKVSCKAPGYTFT | GYDLH | WVRQAPGQGLEWMG | RINPSSGATNYAQRFQG | RVTMTRDVHHHGRHGAEHADI\* |
| D07V | -QVQLVQSGAEVKKPGASVKVSCKAPGYTFT | GYDLH | WVRQAPGQGLEWMG | RINPSSGATNYAQRFQG | RVTMTRD\* |
| D07R | -QVQLVQSGAEVKKPGASVKVSCKAPGYTFT | GYDLH | WVRQAPGQGLEWMG | \* | |
| D07pep[c] | | | | -DVHHHGRHGAEHADI\* | |

TABLE I-continued

Isolated CdS binding sequences and designed mutants (SEQ ID NOS 22-33, respectively, in order of appearance; SEQ ID NOS 19 and 21 are disclosed below the table).

| Clone | FWR1[a,b] | CDR1[b] | FWR2 | CDR2[b] | FWR3[b] |
|---|---|---|---|---|---|
| E01 | -QVQLVQSGAEVKKPGSSVKVSCKASGDTFS | SYAIN | WVRQAPGQGLEWMG | RINPNSGATNYAQRFQG | DVTMTRDVHHHGRHGAEQAEI* |
| E01V | -QVQLVQSGAEVKKPGSSVKVSCKASGDTFS | SYAIN | WVRQAPGQGLEWMG | RINPNSGATNYAQRFQG | RVTMTRD* |
| E01R | -QVQLVQSGAEVKKPGSSVKVSCRASGDTFS | SYAIN | WVRQAPGQGLEWMG | * | |
| E01pep[c] | | | | | -DVHHHGRHGAEQAEI* |

[a]fused to a -(G$_4$S)$_3$AS- linker at the C-terminus of Aga2.
[b]residues in bold differ from contiguous V$_H$ consensus sequences using IgBLAST.
[c]fused directly to a -(G$_4$S)$_3$ASGGG- linker at the C-terminus of Aga2.

TABLE II

Selected Au and FePt binding sequences and designed mutants (SEQ ID NOS 34-52, respectively, in order of appearance; SEQ ID NOS 19 and 21 are disclosed below the table).

| Clone | FWR1[a,b] | CDR1[b] | FWR2[b] | CDR2[b] | FWR3[b] |
|---|---|---|---|---|---|
| Au | | | | | |
| A02 | -QVQLQQSGPGLVKPSQTLSLTCAISGDSVS | SNSAGWT | WIRQSPSRGLEWLG | RTYYKSKWYYDMQYL* | |
| A02Y | -QVQLQQSGPGLVKPSQTLSLTCAISGDSVS | SNSAGWT | WIRQSPSRGLEWLG | RTYYKSKW* | |
| A02S | -QVQLQQSGPGLVKPSQTLSLTCAISGDSVS | SN* | | | |
| A02pep[c] | | | | -YYKSKWYYDMQYL* | |
| A12 | -QVQLQQSGPGLVKPSQTLSLTCAISGDSVS | SNRAAWN | WIRQSPSRGLEWLG | RTYHRSKWGYDMRYL* | |
| A12G | -QVQLQQSGPGLVKPSQTLSLTCAISGDSVS | SNFAAWN | WIRQSPSRGLEWLG | RTYHRSKW* | |
| A12pep[c] | | | | -YHRSKWGYDMRYL* | |
| A01 | -QVQLQQSGPGLVKPSQTLSLTCAISGDSVS | GNTAAWM | WIRQSPSRGLEWLG | RTYYRSKWHYDMRHL* | |
| A01H | -QVQLQQSGPGLVKPSQTLSLTCAISGDSVS | GNTAAWN | WIRQSPSRGLEWLG | RTYYRSKW* | |
| A01pep[c] | | | | -YYRSKWHYDMRHL* | |
| FePt | | | | | |
| G02 | -QVQLVKSEAEVKEPGASVKVSCKASGYTFT | GHYMH | WLRHAPGQGLEWMG | RFNPYSDKLCTEVSGQG | HHDRGHVHQNSLHGAEKAEI* |
| G02H | -QVQLVKSEAEVKEPGASVKVSCKASGYTFT | GHYNH | WLRHAPGQGLEWMG | RFNPYSDKLCTEVSGQG | * |
| G02R | -QVQLVKSEAEVKEPGASVKVSCKASGYTFT | GHYMH | WLRHAPGQGLEWMG | * | |
| G02pep1[c] | | | | | -HHDRGHVHQNSLH* |
| G02pep2[c] | | | | -RFNPYSDKLCTEVSG* | |
| G04 | -QVQLQQSGPGLVKPSQTLSLTCAISGDSVS | THRSAWH | WIRQSPSRGLEWLG | NTYYTSRWYNKLRTEVPG | QSHDYRGQIHEHSLHGAEQPEI* |
| G04Q | -QVQLQQSGPGLVKPSQTLSLTCAISGDSVS | THRSAWH | WIRQSPSRGLEWLG | NTYYTSRWYNKLRTEVPG | * |
| G04N | -QVQLQQSGPGLVKPSQTLSLTCAISGDSVS | THRSAWH | WTRQSPSRGLEWLG | * | |
| G04pep1[c] | | | | -YTSRWYNKLRTEVPG | * |

[a]fused to a -(G$_4$S)$_3$AS- flexible linker at the C-terminus of Aga2.
[b]residues in bold differ from contiguous V$_H$ consensus sequences using IgBLAST.
[c]fused directly to a -(G$_4$S)$_3$ASGGG- linker at the C-terminus of Aga2.

What is claimed is:

1. An isolated or purified composition comprising a plurality of eukaryotic cells, which comprise peptides selected from the group consisting of SEQ ID NOs: 34, 37, 38, 39, 40, 41, and 42, which selectively bind directly to a solid material having a surface.

2. The composition according to claim 1, wherein the solid material having a surface is a crystalline material, a semiconductor material, a metallic material, a magnetic material, a ceramic material, an organic material, an inorganic material or a polymer material having a surface.

3. The composition according to claim 1, wherein the peptides are expressed by the eukaryotic cells.

4. The composition according to claim 1, wherein the peptides are at least one of (i) within and (ii) on the surface of the eukaryotic cells.

5. The composition according to claim 1, wherein the peptides are synthetic.

6. The composition according to claim 1, wherein the solid material comprises $Al_2O_3$, GaN, CdS, Au, FePt, or combinations thereof.

7. The composition according to claim 1, wherein the solid material is Au.

8. The composition according to claim 1, wherein the peptides are scFv peptides.

9. The composition according to claim 1, wherein the eukaryotic cells are selected from the group comprising yeast, insect, plant or mammalian cells.

10. An isolated or purified composition consisting essentially eukaryotic cells, which comprise peptides selected from the group consisting of SEQ ID NOs: 34, 37, 38, 39, 40, 41, and 42, which specifically bind directly to a solid material having a surface and eukaryotic cells, which comprise peptides which do not specifically bind directly to the solid material having a surface.

11. The composition according to claim 10, wherein the eukaryotic cells are yeast cells and the solid material having a surface is a crystalline material, a semiconductor material, a metallic material, a magnetic material, a ceramic material, an organic material, an inorganic material or a polymer material having a surface.

12. The composition according to claim 10, wherein the peptides are synthetic.

13. The composition according to claim 10, wherein the inorganic solid material comprises $Al_2O_3$, GaN, CdS, Au, FePt, or combinations thereof.

14. The composition according to claim 10, wherein the eukaryotic cells are selected from the group comprising yeast, insect, plant or mammalian cells.

15. An isolated or purified host eukaryotic cell comprising one or more peptides selected from the group consisting of SEQ ID NOs: 34, 37, 38, 39, 40, 41, and 42, which selectively bind directly to a solid material having a surface.

16. The cell according to claim 15, wherein the cell is a yeast, insect, plant or mammalian cell, and the material having a surface is a crystalline material, a semiconductor material, a metallic material, a magnetic material, a ceramic material, an organic material, an inorganic material or a polymer material have a surface.

17. A cell covered material comprising one or more eukaryotic cells comprising a peptide selected from the group consisting of SEQ ID NOs: 34, 37, 38, 39, 40, 41, and 42, which selectively bind directly to a solid material having a surface.

18. The material according to claim 17, wherein the eukaryotic cells are yeast, insect, plant or mammalian cells.

19. The material according to claim 17, wherein the solid material having a surface is a crystalline material, a semiconductor material, a metallic material, a magnetic material, a ceramic material, an organic material, an inorganic material or a polymer material have a surface.

20. The material according to claim 17, wherein the material is a self-healing cell-covered material.

21. A method for selective binding of biomolecules from a cell display library to a solid material surface comprising the steps of:
(a) providing a eukaryotic combinatorial cell display library, wherein the library comprises peptides selected from the group consisting of SEQ ID NOs: 34, 37, 38, 39, 40, 41 and 42;
(b) providing a solid material having a surface; and
(c) contacting the cell display library with the solid material having a surface under conditions which result in selective binding of the plurality of expressed biomolecules from the eukaryotic cell display library to the surface.

22. The method according to claim 21, wherein the combinatorial cell display library is a yeast, insect, plant or mammalian cell display library.

23. The method according to claim 21, wherein the solid material having a surface is a crystalline material, a semiconductor material, a metallic material, a ceramic material, an organic material, an inorganic material or a polymer material having a surface.

24. The method according to claim 21, further comprising the step of regulating the expression of the library.

25. The method according to claim 21, further comprising the step of isolating the peptides which selectively bind to the solid material having a surface.

26. A method of growing solid particulate material comprising: mixing one or more precursor reagents for the solid particulate material with one or more eukaryotic cell combinatorial display library members selected for specific binding to the solid particulate material, wherein said eukaryotic cell combinatorial display library members comprise peptides selected from the group consisting of SEQ ID NOs: 34, 37, 38, 39, 40, 41 and 42; wherein said growing is under conditions wherein the solid particulate material is formed in the presence of the one or more eukaryotic combinatorial display library members.

27. The method according to claim 26, wherein the solid particulate material is a nanoparticulate material.

28. The method according to claim 26, wherein the solid particulate is inorganic, organic, magnetic, semiconductor or metallic particulate material.

29. A method of growing particulate solid material comprising:
(a) identifying a peptide selected from the group consisting of SEQ ID NOs: 34, 37, 38, 39, 40, 41 and 42, wherein the peptide is from a eukaryotic cell display library and selectively binds to a solid material; and (b) mixing one or more precursor reagents for the solid material with the peptide under conditions wherein the solid material is formed as a particulate solid material.

30. The method according to claim 29, wherein the eukaryotic cell display library is a yeast or mammalian cell display library.

31. The method according to claim 29, wherein the solid material is an inorganic material.

* * * * *

UNITED STATES PATENT AND TRADEMARK OFFICE
CERTIFICATE OF CORRECTION

| | | |
|---|---|---|
| PATENT NO. | : 8,450,247 B2 | Page 1 of 1 |
| APPLICATION NO. | : 11/051481 | |
| DATED | : May 28, 2013 | |
| INVENTOR(S) | : Peelle et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1718 days.

Signed and Sealed this
Sixteenth Day of December, 2014

Michelle K. Lee
*Deputy Director of the United States Patent and Trademark Office*

SEQUENCE LISTING

<160> NUMBER OF SEQ ID NOS: 52

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Gly Gly Gly Asp Val His His His Gly Arg His Gly Ala Glu His
1               5                   10                  15

Ala Asp Ile

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Asn Lys His Leu Pro Ser Thr Gln Pro Leu Ala
  1               5                  10

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggaactgagc agcctgacta acgaagacac ggccgtc                          37

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gacggccgtg tcttcgttag tcaggctgct cagttcc                          37

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccttgagtgg cagggttaag attaccgcgg acaca                            35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtgtccgcg gtaatcttaa ccctgccact caagg                            35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

-continued caccatgacc agggactaac atcaccacgg ccgac                        35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 8
gtcggccgtg gtgatgttag tccctggtca tggtg                        35

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 9
ggcttgagtg gatgggatag atcaaccccta gcagtgg                     37

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 10
ccactgctag ggttgatcta tcccatccac tcaagcc                      37

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 11
caccatgacc agggactaac atcaccacgg ccgac                        35

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 12
gtcggccgtg gtgatgttag tccctggtca tggtg                        35

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 13
ggcttgagtg gatgggatag atcaaccccta acagtggtg                   39

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caccactgtt agggttgatc tatcccatcc actcaagcc                      39

<210> SEQ ID NO 15
<211> LENGTH: 92
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccggggcta gcggtggcgg ccatgattac agaggtcata ttcatggtca ttctcaacat    60
ggtactgaac aaccagatta ggatccgatc ag                                  92

<210> SEQ ID NO 16
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cccggggcta gcggtggcgg cgatgttcat catcatggta gacatggtgc tgaacatgct    60
gatatttagg atccgatcag                                                80

<210> SEQ ID NO 17
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccggggcta gcggtggcgg cgatgttcat catcatggta gacatggtgc tgaacaagct    60
gaaatttagg atccgatcag                                                80

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atcccggggc tagcggtggc ggc                                       23

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 19

Gly Gly Gly Gly Ser Gly Gly Gly Ser Gly Gly Gly Gly Ser Ala
 1               5                  10                  15

Ser

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Gln or His
<220> FEATURE:
<221> NAME/KEY: MOD_RES
<222> LOCATION: (12)
<223> OTHER INFORMATION: Asp or Glu

<400> SEQUENCE: 20

His His His Gly Arg His Gly Ala Glu Xaa Ala Xaa Ile
 1               5                  10

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser Gly Gly Gly Ser Gly Gly Gly Gly Ser Ala
 1               5                  10                  15

Ser Gly Gly Gly
             20

<210> SEQ ID NO 22
<211> LENGTH: 84
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Gln Gly His Asp Tyr Arg Gly His Ile His Gly His Ser Gln His
     50                  55                  60

Gly Thr Glu Gln Pro Asp Ile Arg Arg His Gly Arg Leu Leu Leu Cys
 65                  70                  75                  80

Glu Arg Cys Asn

<210> SEQ ID NO 23
<211> LENGTH: 70
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 23

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Gln Gly His Asp Tyr Arg Gly His Ile His Gly His Ser Gln His
    50                  55                  60

Gly Thr Glu Gln Pro Asp
 65                  70

<210> SEQ ID NO 24
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Gln Gly
    50

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Asp Tyr Arg Gly His Ile His Gly His Ser Gln His Gly Thr Glu
 1               5                  10                  15

Gln Pro Asp

<210> SEQ ID NO 26
<211> LENGTH: 87
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Val Gln Leu Val Gln Ser Gly Ala Glu Val Lys Lys Pro Gly Ala
 1               5                  10                  15

Ser Val Lys Val Ser Cys Lys Ala Pro Gly Tyr Thr Phe Thr Gly Tyr
            20                  25                  30

Asp Leu His Trp Val Arg Gln Ala Pro Gly Gln Gly Leu Glu Trp Met
        35                  40                  45

Gly Arg Ile Asn Pro Ser Ser Gly Ala Thr Asn Tyr Ala Gln Arg Phe
```

```
                50                  55                  60
Gln Gly Arg Val Thr Met Thr Arg Asp Val His His His Gly Arg His
 65                  70                  75                  80

Gly Ala Glu His Ala Asp Ile
                 85
```

<210> SEQ ID NO 27
<211> LENGTH: 73
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Gln Val Gln Leu Val Gln Ser Gly Ala Glu Val Lys Lys Pro Gly Ala
  1               5                  10                  15

Ser Val Lys Val Ser Cys Lys Ala Pro Gly Tyr Thr Phe Thr Gly Tyr
                 20                  25                  30

Asp Leu His Trp Val Arg Gln Ala Pro Gly Gln Gly Leu Glu Trp Met
             35                  40                  45

Gly Arg Ile Asn Pro Ser Ser Gly Ala Thr Asn Tyr Ala Gln Arg Phe
 50                  55                  60

Gln Gly Arg Val Thr Met Thr Arg Asp
 65                  70
```

<210> SEQ ID NO 28
<211> LENGTH: 49
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Gln Val Gln Leu Val Gln Ser Gly Ala Glu Val Lys Lys Pro Gly Ala
  1               5                  10                  15

Ser Val Lys Val Ser Cys Lys Ala Pro Gly Tyr Thr Phe Thr Gly Tyr
                 20                  25                  30

Asp Leu His Trp Val Arg Gln Ala Pro Gly Gln Gly Leu Glu Trp Met
             35                  40                  45

Gly
```

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Asp Val His His His Gly Arg His Gly Ala Glu His Ala Asp Ile
  1               5                  10                  15
```

<210> SEQ ID NO 30
<211> LENGTH: 87
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
                20                  25                  30

Ala Ile Asn Trp Val Arg Gln Ala Pro Gly Gln Gly Leu Glu Trp Met
            35                  40                  45

Gly Arg Ile Asn Pro Asn Ser Gly Ala Thr Asn Tyr Ala Gln Arg Phe
        50                  55                  60

Gln Gly Arg Val Thr Met Thr Arg Asp Val His His Gly Arg His
65                  70                  75                  80

Gly Ala Glu Gln Ala Glu Ile
                85

<210> SEQ ID NO 31
<211> LENGTH: 73
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
                20                  25                  30

Ala Ile Asn Trp Val Arg Gln Ala Pro Gly Gln Gly Leu Glu Trp Met
            35                  40                  45

Gly Arg Ile Asn Pro Asn Ser Gly Ala Thr Asn Tyr Ala Gln Arg Phe
        50                  55                  60

Gln Gly Arg Val Thr Met Thr Arg Asp
65                  70

<210> SEQ ID NO 32
<211> LENGTH: 49
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
                20                  25                  30

Ala Ile Asn Trp Val Arg Gln Ala Pro Gly Gln Gly Leu Glu Trp Met
            35                  40                  45

Gly

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Val His His His Gly Arg His Gly Ala Glu Gln Ala Glu Ile
1               5                   10                  15

<210> SEQ ID NO 34
<211> LENGTH: 66
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Gly Trp Thr Trp Ile Arg Gln Ser Pro Ser Arg Gly Leu Glu
        35                  40                  45

Trp Leu Gly Arg Thr Tyr Tyr Lys Ser Lys Trp Tyr Tyr Asp Met Gln
    50                  55                  60

Tyr Leu
 65

<210> SEQ ID NO 35
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Gly Trp Thr Trp Ile Arg Gln Ser Pro Ser Arg Gly Leu Glu
        35                  40                  45

Trp Leu Gly Arg Thr Tyr Tyr Lys Ser Lys Trp
    50                  55

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Tyr Lys Ser Lys Trp Tyr Tyr Asp Met Gln Tyr Leu
 1               5                  10

<210> SEQ ID NO 38
<211> LENGTH: 66
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr His Arg Ser Lys Trp Gly Tyr Asp Met Arg
    50                  55                  60

Tyr Leu
 65

<210> SEQ ID NO 39
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr His Arg Ser Lys Trp
    50                  55

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr His Arg Ser Lys Trp Gly Tyr Asp Met Arg Tyr Leu
 1               5                  10

<210> SEQ ID NO 41
<211> LENGTH: 66
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Gly Asn
            20                  25                  30

Thr Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp His Tyr Asp Met Arg
    50                  55                  60

His Leu
 65

<210> SEQ ID NO 42
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Gly Asn
            20                  25                  30

Thr Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp
    50                  55

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Tyr Arg Ser Lys Trp His Tyr Asp Met Arg His Leu
 1               5                  10

<210> SEQ ID NO 44
<211> LENGTH: 86
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Val Gln Leu Val Lys Ser Glu Ala Glu Val Lys Glu Pro Gly Ala
 1               5                  10                  15

Ser Val Lys Val Ser Cys Lys Ala Ser Gly Tyr Thr Phe Thr Gly His
            20                  25                  30

Tyr Met His Trp Leu Arg Arg Ala Pro Gly Gln Gly Leu Glu Trp Met
            35                  40                  45

Gly Arg Phe Asn Pro Tyr Ser Asp Lys Leu Cys Thr Glu Val Ser Gly
    50                  55                  60

Gln Gly His His Asp Arg Gly His Val His Gln Asn Ser Leu His Gly
 65                  70                  75                  80

Ala Glu Lys Ala Glu Ile
                 85

<210> SEQ ID NO 45
<211> LENGTH: 66
<212> TYPE: PRT

<213> ORGANISM: Artificial Sequence
<220> FEATURE:
<223> OTHER INFORMATION: Description of Artificial Sequence: Synthetic peptide

<400> SEQUENCE: 45

Gln Val Gln Leu Val Lys Ser Glu Ala Glu Val Lys Glu Pro Gly Ala
 1               5                  10                  15
Ser Val Lys Val Ser Cys Lys Ala Ser Gly Tyr Thr Phe Thr Gly His
            20                  25                  30
Tyr Met His Trp Leu Arg His Ala Pro Gly Gln Gly Leu Glu Trp Met
        35                  40                  45
Gly Arg Phe Asn Pro Tyr Ser Asp Lys Leu Cys Thr Glu Val Ser Gly
    50                  55                  60
Gln Gly
 65

<210> SEQ ID NO 46
<211> LENGTH: 49
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Gln Val Gln Leu Val Lys Ser Glu Ala Glu Val Lys Glu Pro Gly Ala
 1               5                  10                  15
Ser Val Lys Val Ser Cys Lys Ala Ser Gly Tyr Thr Phe Thr Gly His
            20                  25                  30
Tyr Met His Trp Leu Arg His Ala Pro Gly Gln Gly Leu Glu Trp Met
        35                  40                  45
Gly

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

His His Asp Arg Gly His Val His Gln Asn Ser Leu His
 1               5                  10

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Arg Phe Asn Pro Tyr Ser Asp Lys Leu Cys Thr Glu Val Ser Gly
 1               5                  10                  15

<210> SEQ ID NO 49
<211> LENGTH: 91
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Thr His
            20                  25                  30

Arg Ser Ala Trp His Trp Ile Arg Gln Ser Pro Ser Arg Gly Leu Glu
        35                  40                  45

Trp Leu Gly Asn Thr Tyr Tyr Thr Ser Arg Trp Tyr Asn Lys Leu Arg
    50                  55                  60

Thr Glu Val Pro Gly Gln Ser His Asp Tyr Arg Gly Gln Ile His Glu
65                  70                  75                  80

His Ser Leu His Gly Ala Glu Gln Pro Glu Ile
                85                  90

<210> SEQ ID NO 50
<211> LENGTH: 69
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Thr His
            20                  25                  30

Arg Ser Ala Trp His Trp Ile Arg Gln Ser Pro Ser Arg Gly Leu Glu
        35                  40                  45

Trp Leu Gly Asn Thr Tyr Tyr Thr Ser Arg Trp Tyr Asn Lys Leu Arg
    50                  55                  60

Thr Glu Val Pro Gly
65

<210> SEQ ID NO 51
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Thr His
            20                  25                  30

Arg Ser Ala Trp His Trp Ile Arg Gln Ser Pro Ser Arg Gly Leu Glu
        35                  40                  45

Trp Leu Gly
    50

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Tyr Thr Ser Arg Trp Tyr Asn Lys Leu Arg Thr Glu Val Pro Gly
1               5               10                  15
```